United States Patent
Kato et al.

(10) Patent No.: US 9,518,942 B2
(45) Date of Patent: Dec. 13, 2016

(54) PHASE ANALYZER, PHASE ANALYSIS METHOD, AND SURFACE ANALYZER

(71) Applicant: JEOL Ltd., Tokyo (JP)

(72) Inventors: Naoki Kato, Tokyo (JP); Masaru Takakura, Tokyo (JP); Norihisa Mori, Tokyo (JP); Shinya Fujita, Tokyo (JP); Shigeru Honda, Tokyo (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 14/716,984

(22) Filed: May 20, 2015

(65) Prior Publication Data

US 2015/0362446 A1     Dec. 17, 2015

(30) Foreign Application Priority Data

May 21, 2014  (JP) ................................ 2014-105393

(51) Int. Cl.
| | | |
|---|---|---|
| *G01N 23/222* | (2006.01) | |
| *G01N 23/225* | (2006.01) | |
| *H01J 37/244* | (2006.01) | |

(52) U.S. Cl.
CPC ......... *G01N 23/2252* (2013.01); *H01J 37/244* (2013.01); *H01J 2237/2445* (2013.01); *H01J 2237/2448* (2013.01)

(58) Field of Classification Search
None
See application file for complete search history.

(56) References Cited

U.S. PATENT DOCUMENTS

| | | | | |
|---|---|---|---|---|
| 5,866,903 | A * | 2/1999 | Morita | G01N 23/225 250/307 |
| 8,748,816 | B2 * | 6/2014 | Kooijman | G01N 23/2206 250/305 |
| 2002/0153508 | A1 * | 10/2002 | Lynch | A01N 25/04 252/299.01 |
| 2003/0060836 | A1 * | 3/2003 | Wang | A61B 17/1128 606/152 |
| 2004/0011958 | A1 * | 1/2004 | Wright | G01N 23/203 250/307 |
| 2004/0028815 | A1 * | 2/2004 | Castellano | B01J 19/0046 427/282 |

(Continued)

FOREIGN PATENT DOCUMENTS

JP    2006125952 A  *  5/2006

*Primary Examiner* — Tsung-Yin Tsai
(74) *Attorney, Agent, or Firm* — The Webb Law Firm

(57) ABSTRACT

A phase analyzer includes a principal component analysis section that performs principal component analysis on elemental map data that represents an intensity or concentration distribution corresponding to each element to calculate a principal component score corresponding to each unit area of the elemental map data, a scatter diagram generation section that plots the calculated principal component score to generate a scatter diagram of the principal component score, a peak position detection section that detects a peak position from the scatter diagram, a clustering section that calculates a distance between each point and each peak position within the scatter diagram, and classifies each point within the scatter diagram into a plurality of groups based on the distance, and a phase map generation section that generates a phase map based on classification results of the clustering section.

7 Claims, 26 Drawing Sheets

(56) References Cited

U.S. PATENT DOCUMENTS

| | | | |
|---|---|---|---|
| 2005/0135695 A1* | 6/2005 | Bernard | G06K 9/3233 382/254 |
| 2012/0181425 A1* | 7/2012 | Oohashi | G01N 23/2251 250/307 |
| 2014/0004194 A1* | 1/2014 | Subramanian | A61K 9/08 424/489 |
| 2014/0091216 A1* | 4/2014 | Kinoshita | G01N 23/2252 250/310 |
| 2014/0255772 A1* | 9/2014 | Kyu | H01M 10/052 429/189 |
| 2015/0247908 A1* | 9/2015 | Liu | G01R 33/4804 324/309 |

* cited by examiner

FIG. 3

| PRINCIPAL COMPONENT | CONTRIBUTION RATIO | CUMULATIVE CONTRIBUTION RATIO | EIGENVALUE | EIGENVECTOR ||||||||||
|---|---|---|---|---|---|---|---|---|---|---|---|---|---|
| | | | | Fe | Mn | Al | Ca | O | Si | Ni | Ti | Mg | Cr |
| 1 | 47.09 | 47.09 | 48380.83 | -0.393 | -0.049 | 0.3492 | -0.0988 | 0.1752 | 0.7392 | -0.0015 | -0.0061 | -0.2278 | -0.0011 |
| 2 | 32.93 | 80.02 | 34530.63 | -0.1578 | -0.038 | 0.2672 | 0.5309 | -0.1645 | -0.3836 | -0.0026 | -0.0061 | -0.2597 | -0.0003 |
| 3 | 11.21 | 91.23 | 11747.62 | -0.2206 | 0.0285 | -0.2673 | 0.6738 | -0.0208 | 0.189 | -0.0046 | -0.0681 | 0.5858 | 0 |
| 4 | 4.1 | 95.33 | 4304.07 | 0.7785 | 0.0084 | 0.4088 | 0.1203 | 0.1588 | 0.2713 | -0.007 | 0.0019 | 0.3267 | -0.0002 |
| 5 | 3.47 | 98.8 | 3640.58 | -0.3552 | 0.001 | 0.4 | -0.4226 | 0.8244 | -0.2759 | -0.0015 | -0.0757 | 0.5904 | 0.0002 |
| 6 | 0.94 | 99.74 | 985.11 | 0.0818 | -0.0021 | -0.1674 | 0.2806 | 0.9006 | -0.117 | -0.015 | 0.0189 | -0.2597 | 0.0005 |
| 7 | 0.23 | 99.97 | 241.5 | 0.0031 | 0.0013 | 0.003 | 0.0034 | 0.0148 | 0.0001 | 0.9928 | 0.0012 | 0.0011 | 0 |
| 8 | 0.03 | 100 | 36.47 | -0.1117 | -0.016 | 0.0024 | -0.0027 | -0.0026 | -0.0077 | -0.0006 | 0.9921 | 0.0543 | 0.002 |
| 9 | 0 | 100 | 0.34 | -0.0084 | 0.999 | 0.00008 | -0.0008 | 0.0005 | -0.0007 | -0.0013 | 0.0155 | -0.0071 | -0.0413 |
| 10 | 0 | 100 | 0.12 | -0.0004 | 0.0413 | 0.0008 | 0.0001 | -0.0006 | 0.001 | 0 | -0.0013 | -0.0007 | 0.9991 |

FIG.17

| 0 | 0 | 0 | 1 | 3 | 11 | 8 |
|---|---|---|---|---|---|---|
| 2 | 2 | 4 | 5 | 6 | 7 | 9 |
| 2 | 1 | 5 | 14 | 26 | 11 | 13 |
| 1 | 8 | 11 | 24 | 31 | 11 | 12 |
| 0 | 12 | 18 | 25 | 29 | 11 | 8 |
| 3 | 1 | 11 | 23 | 24 | 9 | 5 |

PHASE ANALYZER, PHASE ANALYSIS METHOD, AND SURFACE ANALYZER

Japanese Patent Application No. 2014-105393 filed on May 21, 2014, is hereby incorporated by reference in its entirety.

BACKGROUND OF THE INVENTION

The present invention relates to a phase analyzer, a phase analysis method, and a surface analyzer.

Phase analysis has been known as a method that analyzes elemental map data (intensity or concentration distribution data corresponding to each element) acquired using a surface analyzer such as an electron probe microanalyzer (EPMA). The term "phase analysis" refers to a method that extracts the phase of a compound from the correlation between a plurality of elements, and determines the correlation corresponding to each phase. For example, JP-A-2006-125952 discloses a surface analyzer that implements phase analysis that generates a scatter diagram based on concentration distribution data relating to a plurality of elements obtained from the area analysis results to estimate the presence of a compound or the like.

A process that generates a phase map (i.e., a diagram that shows the compound distribution) from elemental map data normally includes a map analysis (area analysis) step, an elemental map data readout step, a scatter diagram generation step, an uneven data distribution search step (that searches the scatter diagram for an uneven data distribution), and a phase map generation step. Each step is described below.

The map analysis step performs map analysis using a surface analyzer. The map analysis is performed by dividing a specified range of a sample into pixels (unit areas), and measuring the X-ray intensity at each pixel, for example. The elemental map data obtained by the map analysis is displayed as an image that represents the difference in X-ray intensity using a color (i.e., the difference in brightness or hue). FIG. 21 illustrates Al elemental map data, and FIG. 22 illustrates Ca elemental map data.

The elemental map data readout step reads the elemental map data by causing a computer to execute phase analysis software. The elemental map data of each element is read as intensity data having one column. For example, the elemental map data analyzed using 300×300 pixels has 90,000 rows.

In the scatter diagram generation step, the phase analysis software generates the scatter diagram based on the elemental map data. For example, when the user has selected two pieces of elemental map data from a plurality of pieces of elemental map data (that have been read), the phase analysis software plots the intensity data at each point of a scatter diagram in which the horizontal axis indicates one of the two pieces of elemental map data selected by the user, and the vertical axis indicates the other of the two pieces of elemental map data selected by the user. FIG. 23 illustrates a scatter diagram in which the horizontal axis indicates Al elemental map data, and the vertical axis indicates Ca elemental map data.

In the uneven data distribution search step, an uneven distribution is determined by changing the display color of the scatter diagram corresponding to the number of data points (see FIG. 24). In the example illustrated in FIG. 24, five uneven distributions are observed within the scatter diagram.

The phase map generation step encloses each uneven distribution, and applies a different color to each uneven distribution (see FIG. 25). Each color is reflected in the display state of the elemental map data to generate the phase map (see FIG. 26).

According to the above process, however, a number of steps are required to generate the phase map. In particular, the user must select an appropriate combination of elements from a large number of elements in the scatter diagram generation step, and determine the correlation between the elements. It is difficult for an inexperienced user to select an appropriate combination of elements, and determine the correlation between the elements. For example, it is necessary to try a large number of combinations (up to forty-five combinations when the number of pieces of elemental map data is 10) in order to find the most useful combination from ten pieces of elemental map data.

SUMMARY

Several aspects of the invention may provide a phase analyzer and a phase analysis method that can easily generate the phase map as well as a surface analyzer that includes the phase analyzer.

According to a first aspect of the invention, there is provided a phase analyzer including:

a principal component analysis section that performs principal component analysis on elemental map data that represents an intensity or concentration distribution corresponding to each element to calculate a principal component score corresponding to each unit area of the elemental map data;

a scatter diagram generation section that plots the calculated principal component score to generate a scatter diagram of the principal component score;

a peak position detection section that detects a peak position from the scatter diagram;

a clustering section that calculates a distance between each point and each peak position within the scatter diagram, and classifies each point within the scatter diagram into a plurality of groups based on the distance; and a phase map generation section that generates a phase map based on classification results of the clustering section.

According to a second aspect of the invention, there is provided a phase analysis method including:

a principal component analysis step that performs principal component analysis on elemental map data that represents an intensity or concentration distribution corresponding to each element to calculate a principal component score corresponding to each unit area of the elemental map data;

a scatter diagram generation step that plots the calculated principal component score to generate a scatter diagram of the principal component score;

a peak position detection step that detects a peak position from the scatter diagram;

a clustering step that calculates a distance between each point and each peak position within the scatter diagram, and classifies each point within the scatter diagram into a plurality of groups based on the distance; and a phase map generation step that generates a phase map based on classification results of the clustering step.

According to a third aspect of the invention, there is provided a surface analyzer including the above phase analyzer.

BRIEF DESCRIPTION OF THE SEVERAL VIEWS OF THE DRAWING

FIG. 3 is a table illustrating the results of principal component analysis.

FIG. 17 illustrates part of data of a scatter diagram displayed using point density.

Figure 1:
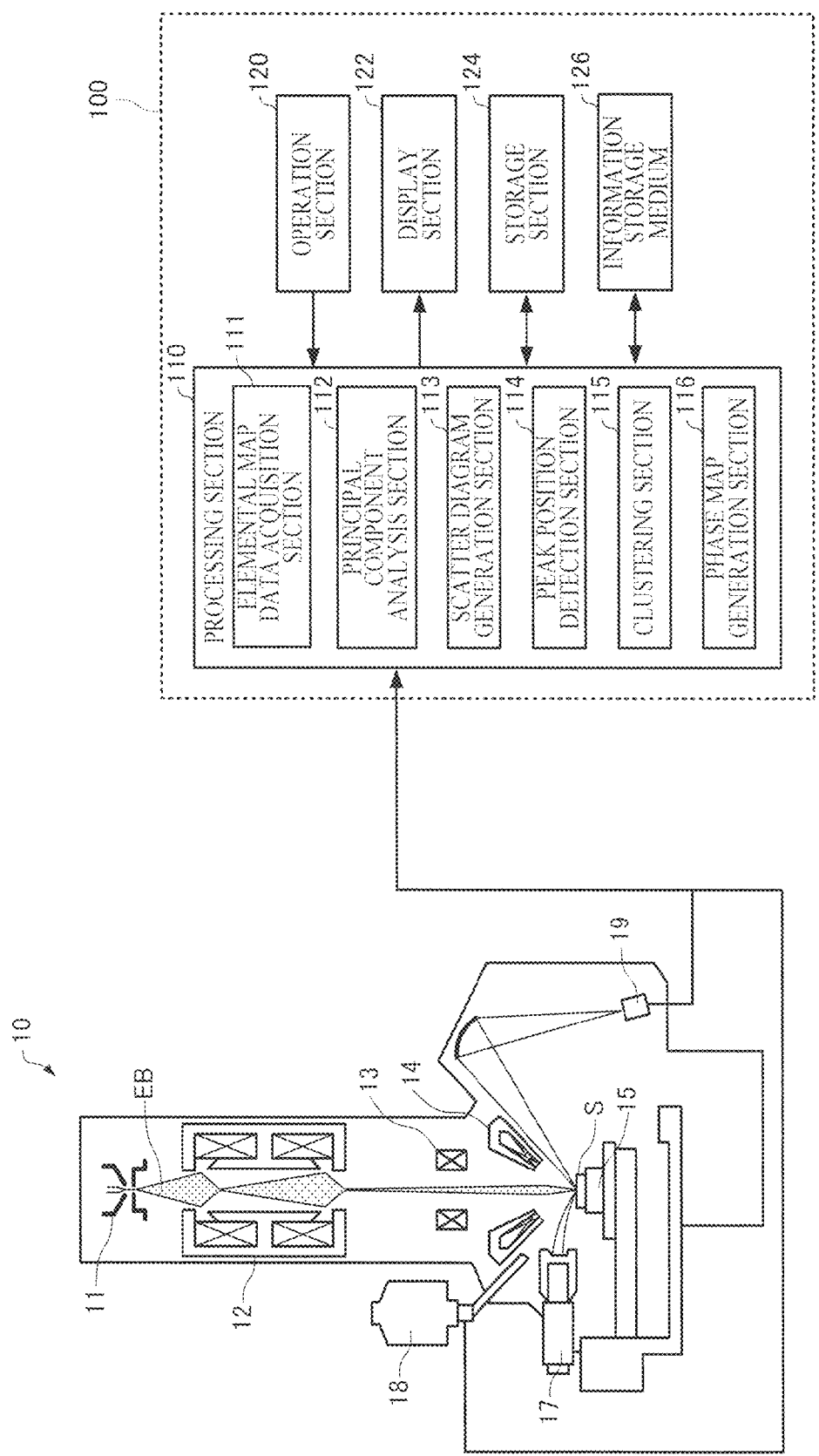
FIG. 1 schematically illustrates the configuration of a surface analyzer that includes a phase analyzer according to one embodiment of the invention.

DETAILED DESCRIPTION OF THE EMBODIMENT (1) A phase analyzer according to one embodiment of the invention includes:

a principal component analysis section that performs principal component analysis on elemental map data that represents an intensity or concentration distribution corresponding to each element to calculate a principal component score corresponding to each unit area of the elemental map data;

a scatter diagram generation section that plots the calculated principal component score to generate a scatter diagram of the principal component score;

a peak position detection section that detects a peak position from the scatter diagram;

a clustering section that calculates a distance between each point and each peak position within the scatter diagram, and classifies each point within the scatter diagram into a plurality of groups based on the distance; and a phase map generation section that generates a phase map based on classification results of the clustering section.

According to this configuration, the user need not select an appropriate combination of elements from a large number of elements and determine the correlation between the elements, and it is possible to easily generate the phase map, for example.

Since the phase analyzer utilizes the principal component analysis, it is possible to easily generate the phase map while utilizing information about a larger number of elements as compared with the case of selecting a small number of elements from a large number of elements, and performing phase analysis based on the correlation between the selected elements.

(2) In the phase analyzer, the peak position detection section may divide the scatter diagram into a plurality of areas, count the number of data points within each of the plurality of areas to calculate the point density, and detect the peak position based on the point density.

This makes it possible to detect the peak position (i.e., the center of gravity of each cluster) from the principal component score scatter diagram.

(3) In the phase analyzer, the peak position detection section may determine an area among contiguous areas included in the plurality of areas that has the highest point density to be a peak position candidate, and select the peak position candidate in which the point density is equal to or higher than a threshold value to be the peak position.

This makes it possible to perform the peak position narrow-down process using the peak position detection section.

(4) In the phase analyzer, the clustering section may classify each point within the scatter diagram so that each point belongs to a group among the plurality of groups that corresponds to the peak position that is situated at the shortest distance from each point.

This makes it possible to classify each point within the principal component score scatter diagram corresponding to the composition using the clustering section.

(5) In the phase analyzer, the phase map generation section may display the phase map on a display section in a state in which each point within the phase map is color-coded corresponding to each of the plurality of groups.

The phase analyzer can thus comprehensibly display the phase distribution.

(6) A phase analysis method according to another embodiment of the invention includes:

a principal component analysis step that performs principal component analysis on elemental map data that represents an intensity or concentration distribution corresponding to each element to calculate a principal component score corresponding to each unit area of the elemental map data;

a scatter diagram generation step that plots the calculated principal component score to generate a scatter diagram of the principal component score;

a peak position detection step that detects a peak position from the scatter diagram;

a clustering step that calculates a distance between each point and each peak position within the scatter diagram, and classifies each point within the scatter diagram into a plurality of groups based on the distance; and a phase map generation step that generates a phase map based on classification results of the clustering step.

According to this configuration, the user need not select an appropriate combination of elements from a large number of elements and determine the correlation between the elements, and it is possible to easily generate the phase map, for example.

Since the phase analysis method utilizes the principal component analysis, it is possible to easily generate the phase map while utilizing information about a larger number of elements as compared with the case of selecting a small number of elements from a large number of elements, and performing phase analysis based on the correlation between the selected elements.

(7) In the phase analysis method, the peak position detection step may divide the scatter diagram into a plurality of areas, count the number of data points within each of the plurality of areas to calculate the point density, and detect the peak position based on the point density.

This makes it possible to detect the peak position (i.e., the center of gravity of each cluster) from the principal component score scatter diagram.

(8) In the phase analysis method, the peak position detection step may determine an area among contiguous areas included in the plurality of areas that has the highest point density to be a peak position candidate, and select the peak position candidate in which the point density is equal to or higher than a threshold value to be the peak position.

This makes it possible to perform the peak position narrow-down process by performing the peak position detection step.

(9) In the phase analysis method, the clustering step may classify each point within the scatter diagram so that each point belongs to a group among the plurality of groups that corresponds to the peak position that is situated at the shortest distance from each point.

This makes it possible to classify each point within the principal component score scatter diagram corresponding to the composition in the clustering step.

(10) In the phase analysis method, the phase map generation step may display the phase map on a display section in a state in which each point within the phase map is color-coded corresponding to each of the plurality of groups.

The phase analysis method can thus comprehensibly display the phase distribution.

(11) A surface analyzer according to another embodiment of the invention includes the phase analyzer.

Since the surface analyzer includes the phase analyzer, the surface analyzer can easily generate the phase map.

Exemplary embodiments of the invention are described in detail below with reference to the drawings. Note that the following exemplary embodiments do not unduly limit the scope of the invention as stated in the claims. Note also that all of the elements described in connection with the following exemplary embodiments should not necessarily be taken as essential elements of the invention.

1. Phase Analyzer

A phase analyzer according to one embodiment of the invention is described below with reference to the drawings. FIG. 1 is a view schematically illustrating the configuration of a surface analyzer 1000 that includes a phase analyzer 100 according to one embodiment of the invention. Note that the phase analyzer 100 need not necessarily be included in the surface analyzer 1000.

As illustrated in FIG. 1, the surface analyzer 1000 includes a surface analyzer main body 10 in addition to the phase analyzer 100.

The surface analyzer 1000 applies electron beams EB to a sample S, detects characteristic X-rays that are emitted (generated) from the sample S when the electron beams EB have been applied to the sample S, and qualitatively or quantitatively analyzes an element included in the sample S. The surface analyzer 1000 can perform area analysis (map analysis) on the sample S. The surface analyzer 1000 is an electron probe microanalyzer (EPMA), for example.

The surface analyzer main body 10 includes an electron gun 11, a condenser lens 12, a deflector 13, an objective lens 14, a sample stage 15, a secondary electron detector 17, an energy-dispersive detector 18, and a wavelength-dispersive detector 19.

The electron gun 11 generates the electron beams EB. The electron gun 11 emits the electron beams EB that have been accelerated by applying a predetermined accelerating voltage toward the sample S.

The condenser lens 12 is disposed in the subsequent stage of the electron gun 11 (on the downstream side of the electron gun 11 (that emits the electron beams EB)). The condenser lens 12 focuses the electron beams EB.

The deflector 13 is disposed in the subsequent stage of the condenser lens 12. The deflector 13 deflects the electron beams EB. A scan signal is input to the deflector 13 through a control circuit (not illustrated in FIG. 1) so that the sample S is scanned with the electron beams EB that have been focused by the condenser lens 12 and the objective lens 14.

The objective lens 14 is disposed in the subsequent stage of the deflector 13. The objective lens 14 focuses the electron beams EB on the sample S to apply the electron beams EB to the sample S as an electronic probe.

The sample stage 15 supports the sample S. The sample S is placed on the sample stage 15. The sample stage 15 is moved by a stage-moving mechanism (not illustrated in FIG. 1) that includes a drive source (e.g., motor). The analysis position (analysis area (part)) on the sample S to which the electron beams EB (electronic probe) are applied can be relatively moved by moving the sample stage 15.

The secondary electron detector 17 detects secondary electrons released from the sample S. The secondary electron detector 17 is an Everhart-Thornley detector (ET detector), for example. A secondary electron image (SEM image) can be obtained from the measurement results (output signal) of the secondary electron detector 17. The signal output from the secondary electron detector 17 is stored (recorded) in a storage section 124 as image data that is synchronized with the scan signal for the electron beams EB, for example.

The energy-dispersive detector 18 (energy-dispersive X-ray spectrometer) detects X-rays based on energy to obtain a spectrum. The energy-dispersive detector 18 detects the characteristic X-rays that are generated when the electron beams EB have been applied to the sample S.

The wavelength-dispersive detector 19 separates and detects the characteristic X-rays that are generated when the electron beams EB have been applied to the sample S. The wavelength-dispersive detector 19 separates X-rays having a specific wavelength by utilizing Bragg reflection of X-rays due to an analyzing crystal, for example.

The surface analyzer main body 10 can perform map analysis (area analysis) on the sample S. Specifically, the surface analyzer main body 10 divides a specific range of the sample S into pixels (unit areas), and measures the X-ray intensity at each pixel using the energy-dispersive detector 18 or the wavelength-dispersive detector 19 to obtain elemental map data (elemental distribution information). The elemental map data includes two-dimensional distribution information about an element. The elemental map data includes information about the two-dimensional position (coordinates) and the X-ray intensity (or concentration) at each position. The elemental map data is obtained corresponding to each element. The elemental map data output from the surface analyzer main body 10 is stored in the storage section 124 included in the phase analyzer 100, for example.

The phase analyzer 100 acquires the elemental map data obtained by the map analysis performed by the surface analyzer main body 10, and performs phase analysis. The term "phase analysis" used herein refers to a method that extracts the phase of a compound from the correlation between a plurality of elements, and determines the correlation corresponding to each phase. The phase analyzer 100 is implemented by a general-purpose computer such as a personal computer (PC), for example. The phase analyzer 100 includes a processing section 110, an operation section 120, a display section 122, the storage section 124, and an information storage medium 126.

The operation section 120 acquires an operation signal that corresponds to the operation performed by the user, and transmits the operation signal to the processing section 110. The operation section 120 is implemented by a button, a key, a touch panel display, or a microphone, for example.

The display section 122 displays an image generated by the processing section 110. The function of the display section 122 may be implemented by an LCD, a CRT, or the like. The display section 122 displays a phase map generated by the processing section 110 (phase map generation section 116), for example. The display section 122 also displays the secondary electron image, the elemental map, and the like.

The storage section 124 serves as a work area for the processing section 110. The function of the storage section 124 may be implemented by a RAM or the like. The storage section 124 stores a program, data, and the like that cause or allow the processing section 110 to perform various calculation processes and control processes. The storage section 124 is used as a work area for the processing section 110, and temporarily stores the results of calculations performed by the processing section 110 according to a program, and the like.

The storage section 124 stores information about the size of an area used when a peak position detection section 114 (described later) divides a principal component score scatter diagram into a plurality of areas, and information about a condition (information about a threshold value) used when narrowing down the peak positions, for example. The storage section 124 also stores a list of phase colors used when a phase map generation section 116 generates a phase map, for example. The storage section 124 also stores information about the eigenvalue of each principal component and the eigenvector of each element (see FIG. 3), information about the principal component score scatter diagram (see FIGS. 15 and 18), and information about the phase map (see FIG. 19), for example.

The information storage medium 126 (computer-readable medium) stores a program, data, and the like. The function of the information storage medium 126 may be implemented by an optical disk (CD or DVD), a magneto-optical disk (MO), a magnetic disk, a hard disk, a magnetic tape, a memory (ROM), or the like. The processing section 110 performs various processes according to one embodiment of the invention based on the program (data) stored in the information storage medium 126. The information storage medium 126 may store a program that causes a computer to function as each section of the processing section 110.

The processing section 110 performs various calculation processes according to the program stored in the storage section 124. The processing section 110 functions as an elemental map data acquisition section 111, a principal component analysis section 112, a scatter diagram generation section 113, a peak position detection section 114, a clustering section 115, and a phase map generation section 116 by executing the program stored in the storage section 124. The function of the processing section 110 may be implemented by hardware such as processor (e.g., CPU or DSP) or ASIC (e.g., gate array), or a program. Note that at least part of the processing section 110 may be implemented by hardware (dedicated circuit). The processing section 110 includes the elemental map data acquisition section 111, the principal component analysis section 112, the scatter diagram generation section 113, the peak position detection section 114, the clustering section 115, and the phase map generation section 116.

Figure 2:
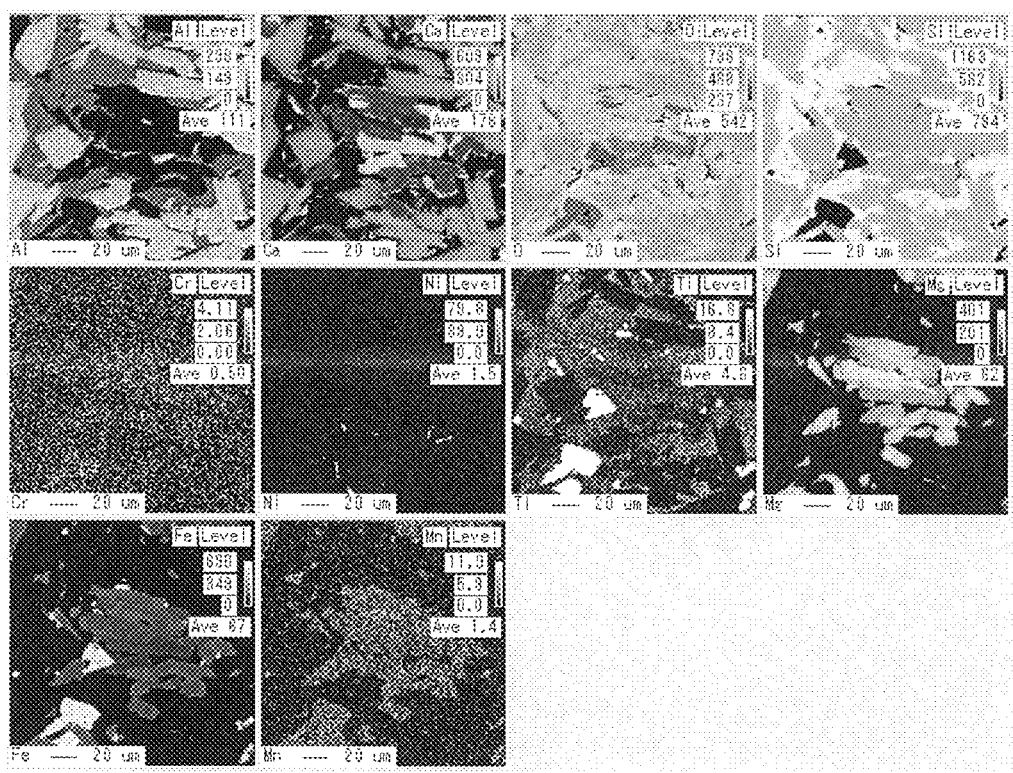
FIG. 2 illustrates an example of elemental map data acquired by an elemental map data acquisition section.

The elemental map data acquisition section 111 acquires a plurality of pieces of elemental map data. For example, when the user has selected some pieces of elemental map data from a plurality of pieces of elemental map data obtained by the area analysis performed by the surface analyzer main body 10, the elemental map data acquisition section 111 reads the selected elemental map data from the storage section 124. The user selects the desired elemental map data from a plurality of pieces of elemental map displayed on the display section 122, for example. FIG. 2 is a view illustrating an example of the elemental map data acquired by the elemental map data acquisition section 111. In the example illustrated in FIG. 2, Al elemental map data, Ca elemental map data, O elemental map data, Si elemental map data, Mn elemental map data, Fe elemental map data, Ni elemental map data, Ti elemental map data, Mg elemental map data, and Cr elemental map data have been acquired by the elemental map data acquisition section 111.

For example, the elemental map data acquisition section 111 reads each piece of elemental map data as intensity data (or concentration data) having one column. For example, the elemental map data analyzed using 300×300 pixels has 90,000 rows.

The principal component analysis section 112 performs principal component analysis on the elemental map data acquired by the elemental map data acquisition section 111 to calculate the principal component score corresponding to each pixel (unit area) of the elemental map data.

The term "principal component analysis" refers to a multivariate analysis (statistics) method that calculates a small number of characteristic variables (composite variables) from multivariate data, the characteristic variables representing the characteristics of the data set. The composite variable (principal component) u is represented by the following expression.

$$u_i = a_1 x_{1,i} + a_2 x_{2,i} + \ldots + a_{N-1} x_{N-1,i} + a_N x_{N,i}$$

where, N is the number of variables, i is a natural number, x is data of each variable, and $a_1, a_2 \ldots a_{N-1}$, and $a_n$ are composite variable coefficients.

The composite variable coefficients $a_1, a_2 \ldots a_{N-1}$, and $a_N$ are calculated so that the variance of the composite variable u becomes a maximum. Note that the composite variable coefficients satisfy the following relationship.

$$a_1^2 + a_2^2 + \ldots + a_{N-1}^2 + a_N^2 = 1$$

When calculating the composite variable coefficients $a_1, a_2 \ldots a_{N-1}$, and $a_N$, the variance-covariance matrix of the original data set is calculated, and the eigenvalue problem of the variance-covariance matrix is solved. The eigenvector that is the solution to the eigenvalue problem corresponds to the coefficients $a_1, a_2 \ldots a_{N-1}$, and $a_N$. The resulting N (i.e., the same number as the number of pieces of data included in the original data set) principal components include a first principal component, a second principal component . . . and an Nth principal component (in descending order of the eigenvalue).

The principal component analysis section 112 performs the principal component analysis on the data (intensity value or concentration value) of each pixel of the elemental map data acquired by the elemental map data acquisition section 111. FIG. 3 illustrates a table that shows the results of the principal component analysis. As illustrated in FIG. 3, information about the contribution ratio, the cumulative contribution ratio, the eigenvalue, and the eigenvector is obtained corresponding to each principal component as a result of the principal component analysis performed by the principal component analysis section 112. When the principal component analysis section 112 has performed the principal component analysis on ten pieces of elemental map data (see FIG. 2), information about a first principal component to a tenth principal component is obtained (see FIG. 3).

The principal component analysis section 112 calculates the principal component score corresponding to each pixel of each elemental map data using the eigenvector (see FIG. 3). The principal component analysis section 112 thus generates a principal component score map data corresponding to each principal component. The principal component score may be calculated using the following expression.

$$u_i = a_1(x_{1,i} - \bar{x}_1) + a_2(x_{2,i} - \bar{x}_2) + \ldots + a_N(x_{N,i} - \bar{x}_N)$$

where, a is the eigenvector, x is the data (intensity value or concentration value) of each pixel, i is 1 to the total number of pixels, N is the total number of elements, and $\bar{x}_k$ is the average value (average intensity value or average concentration value) of each elemental map data.

Note that the average value of each elemental map data is subtracted from the data of each pixel so that the principal component score corresponds to the origin 0 when the data of each pixel corresponds to the average value.

For example, the principal component score of the first principal component (first principal component score) can be calculated by the following expression using the results of the principal component analysis in FIG. 3.

$$u_1 = -0.393 \times (Fe - \overline{Fe}) - 0.0049 \times (Mn - \overline{Mn}) + 0.3492 \times (Al - \overline{Al}) - 0.0388 \times (Ca - \overline{Ca}) + 0.1753 \times (O - \overline{O}) + 0.7992 \times (Si - \overline{Si}) - 0.0015 \times (Ni - \overline{Ni}) - 0.0261 \times (Ti - \overline{Ti}) - 0.2278 \times (Mg - \overline{Mg}) - 0.0011 \times (Cr - \overline{Cr})$$

where, "Fe" is the data (intensity value or concentration value) of each pixel of the Fe elemental map data, and "$\overline{Fe}$" is the average value of the data (intensity value or concentration value) of each pixel of the Fe elemental map data. These definitions also apply to the other elements.

Figure 4:
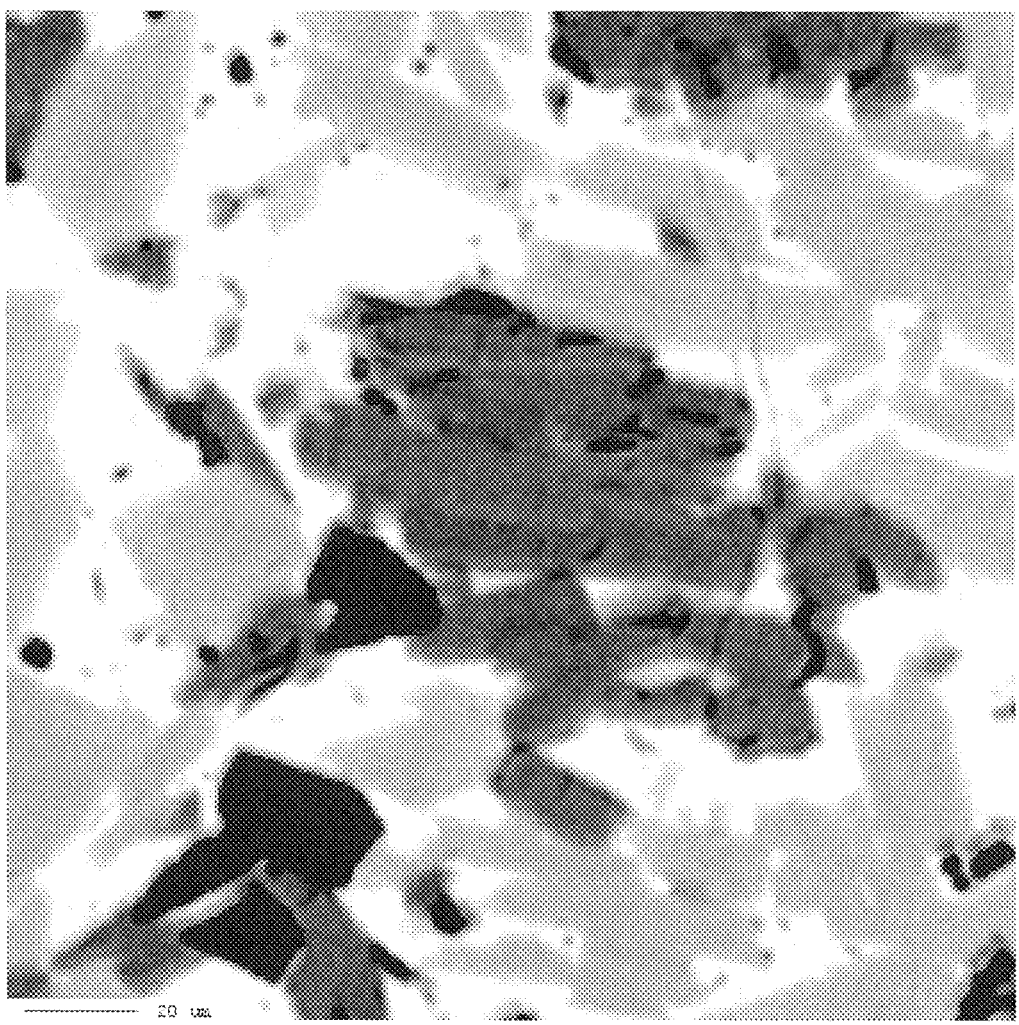
FIG. 4 illustrates principal component score map data of a first principal component score.

The principal component analysis section 112 generates the principal component score map data of the first principal component from the data of the principal component score calculated corresponding to each pixel using the above expression. The principal component score map data represents the principal component score calculated corresponding to each pixel in the form of map data (i.e., data that represents the position and the principal component score at the corresponding position). FIG. 4 illustrates principal component score map data of the first principal component score.

Figure 5:
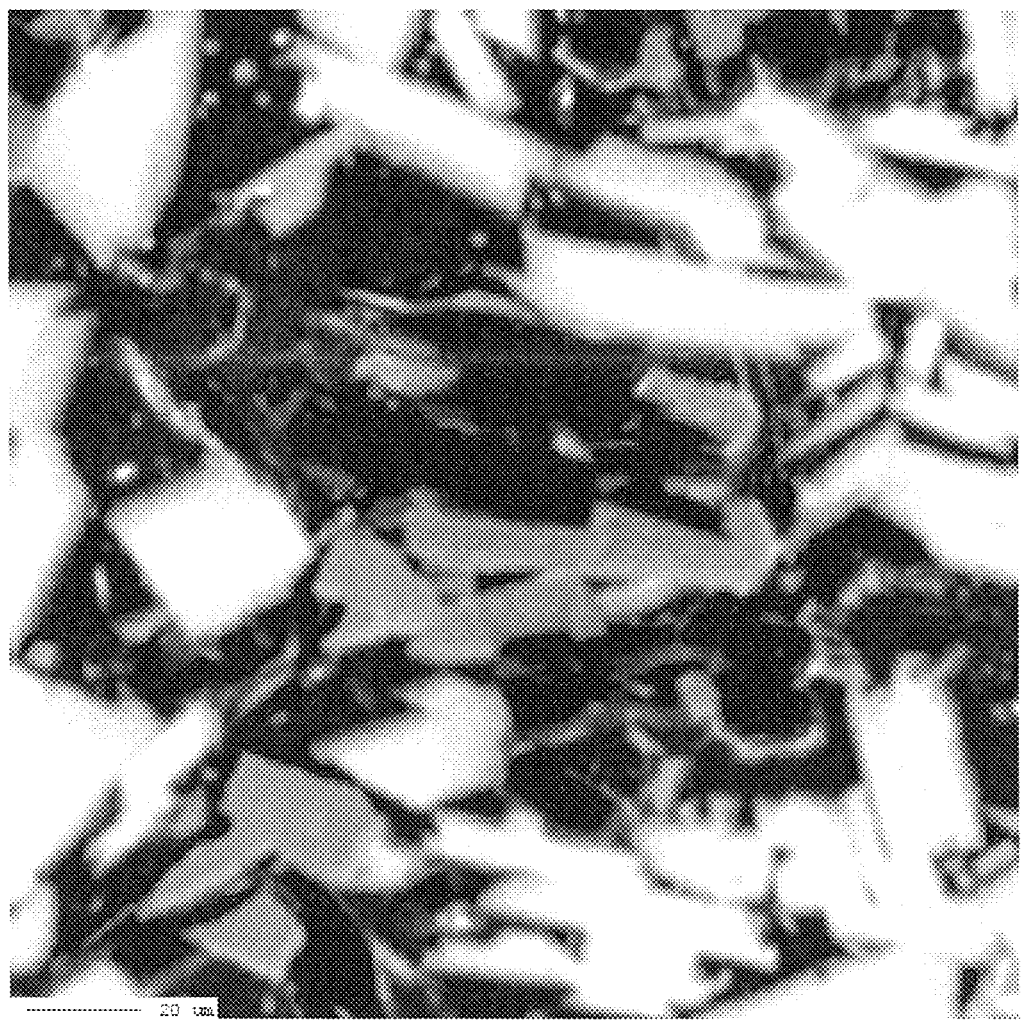
FIG. 5 illustrates principal component score map data of a second principal component score.
Figure 6:
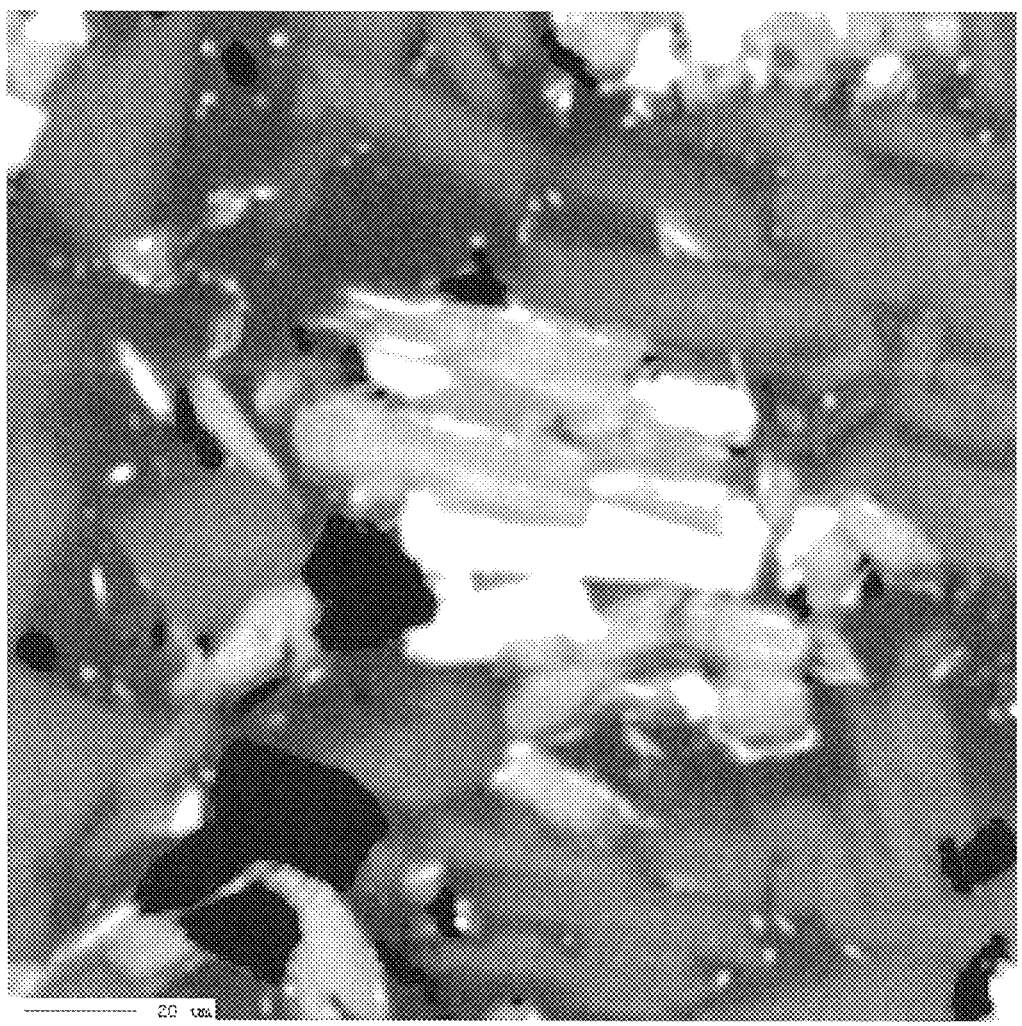
FIG. 6 illustrates principal component score map data of a third principal component score.
Figure 7:
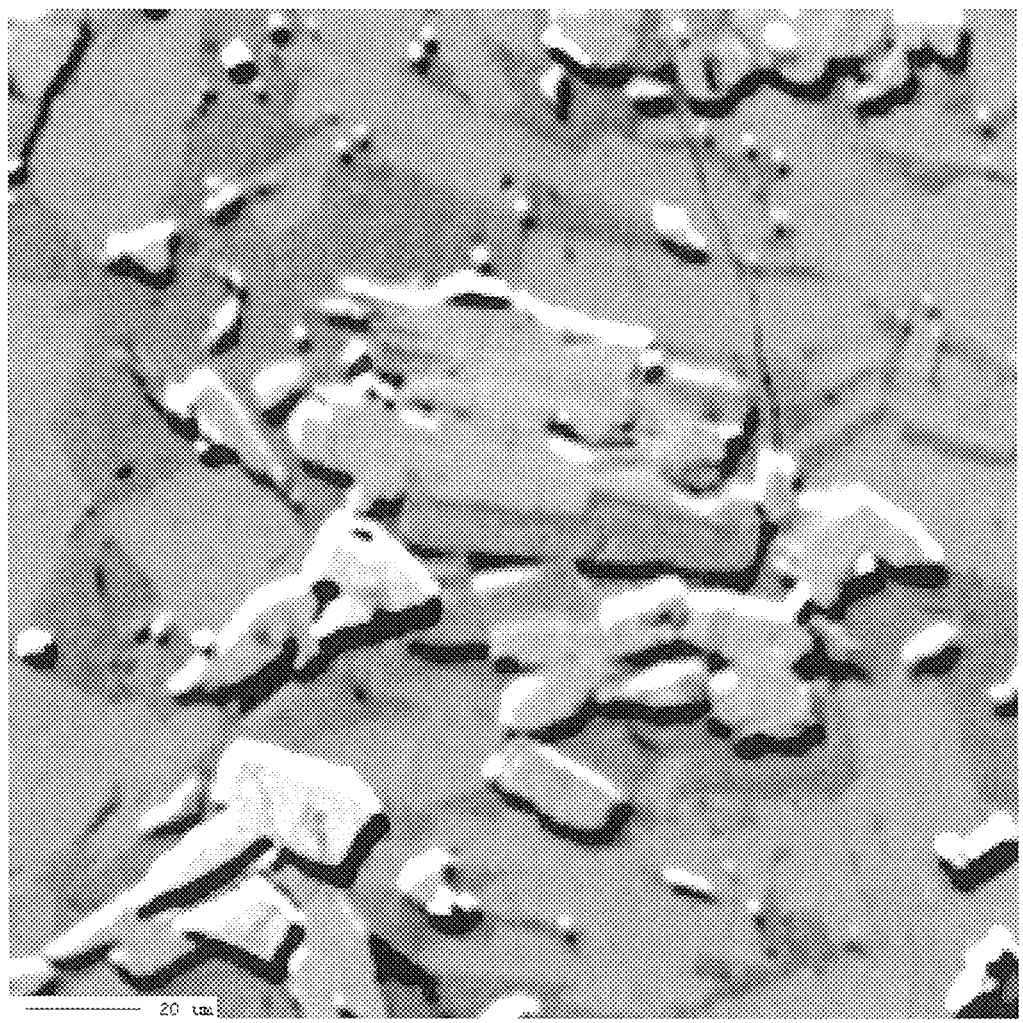
FIG. 7 illustrates principal component score map data of a fourth principal component score.
Figure 8:
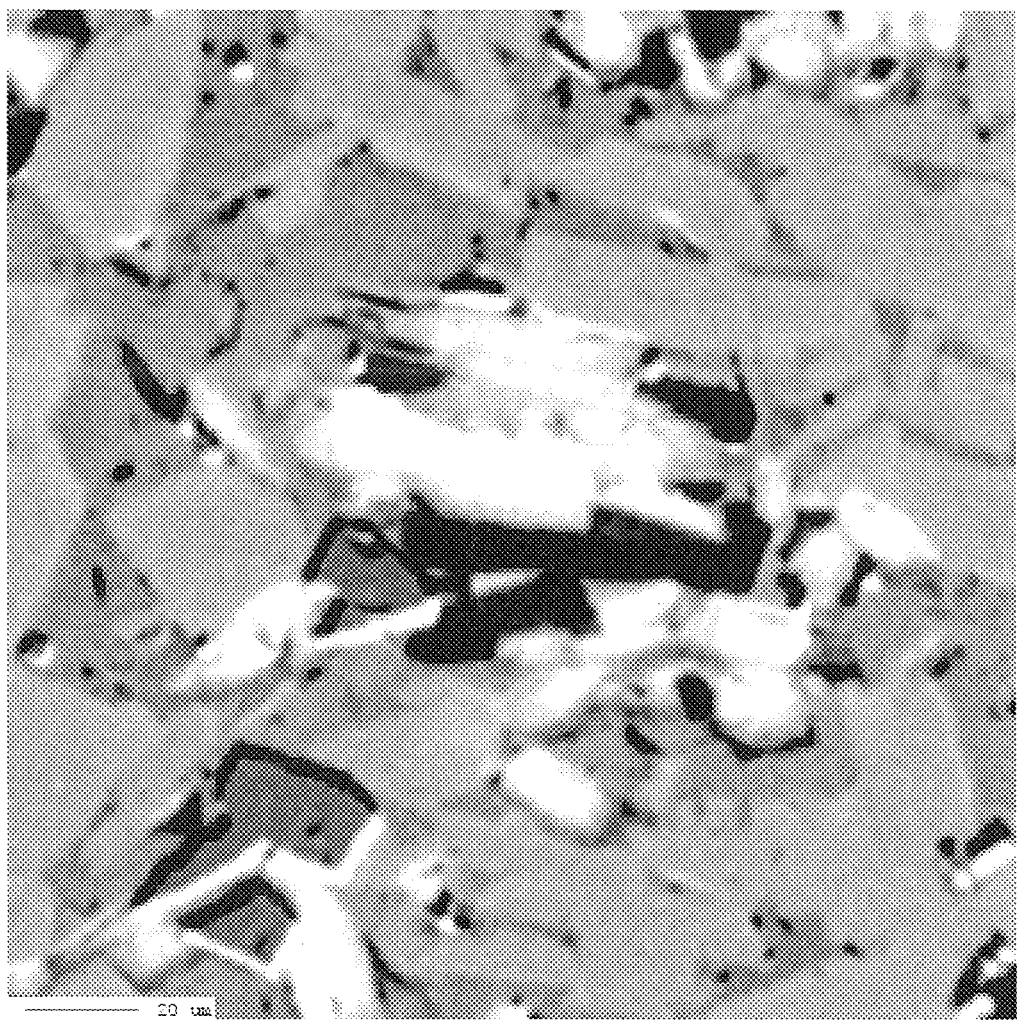
FIG. 8 illustrates principal component score map data of a fifth principal component score.
Figure 9:
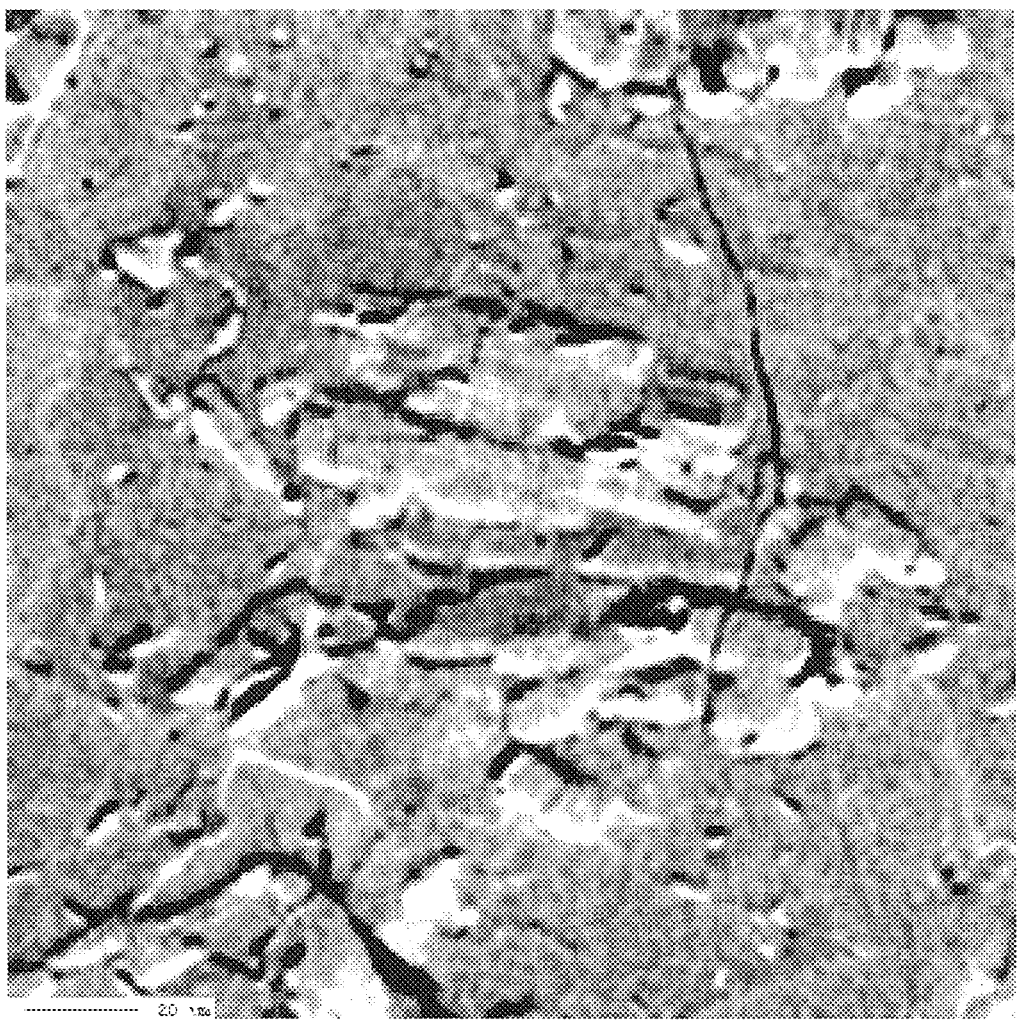
FIG. 9 illustrates principal component score map data of a sixth principal component score.
Figure 10:
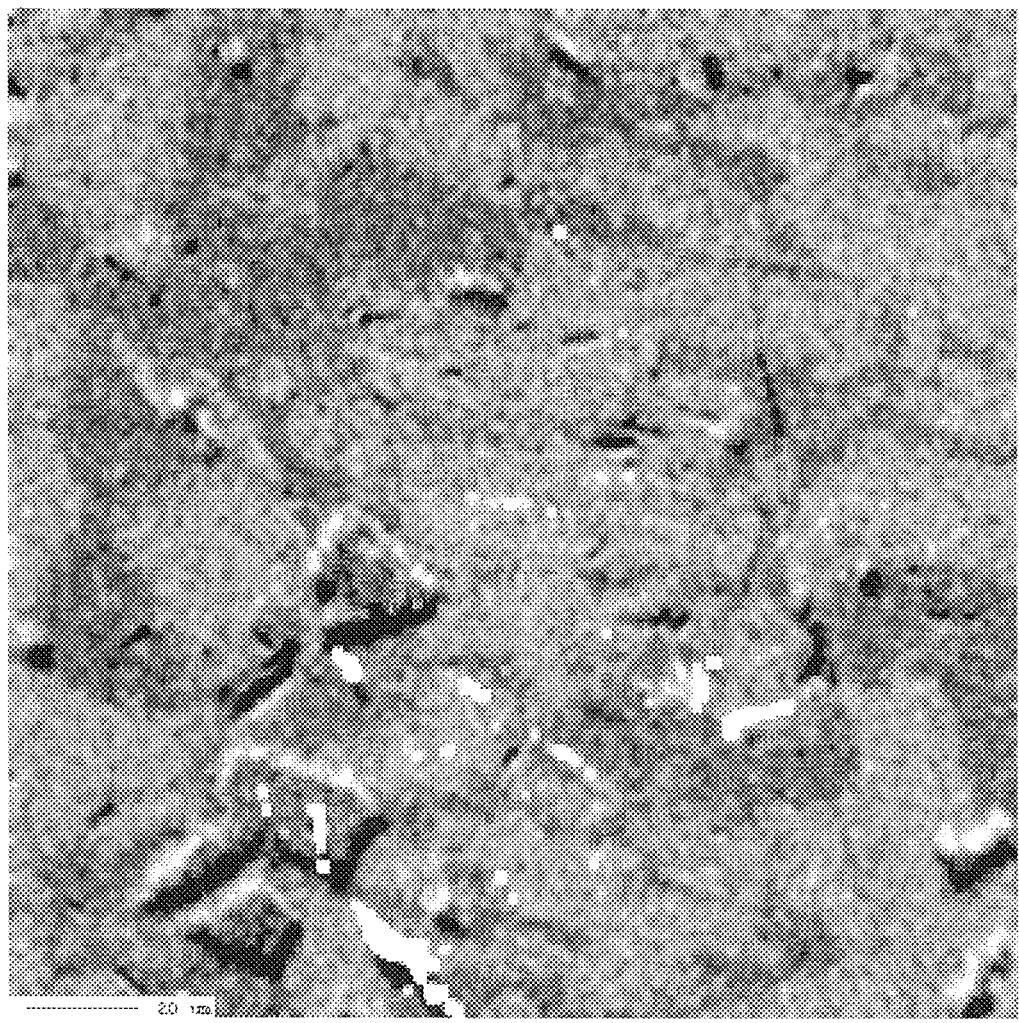
FIG. 10 illustrates principal component score map data of a seventh principal component score.
Figure 11:
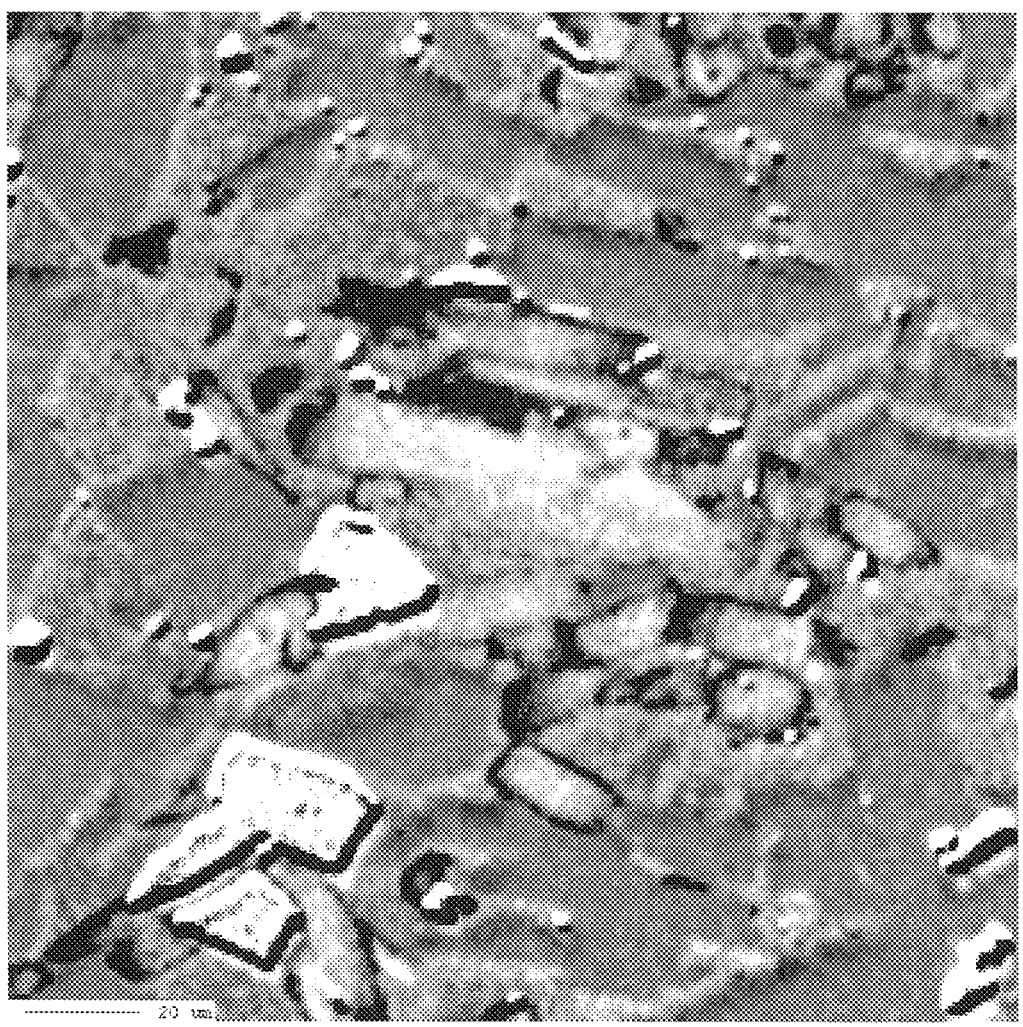
FIG. 11 illustrates principal component score map data of an eighth principal component score.
Figure 12:
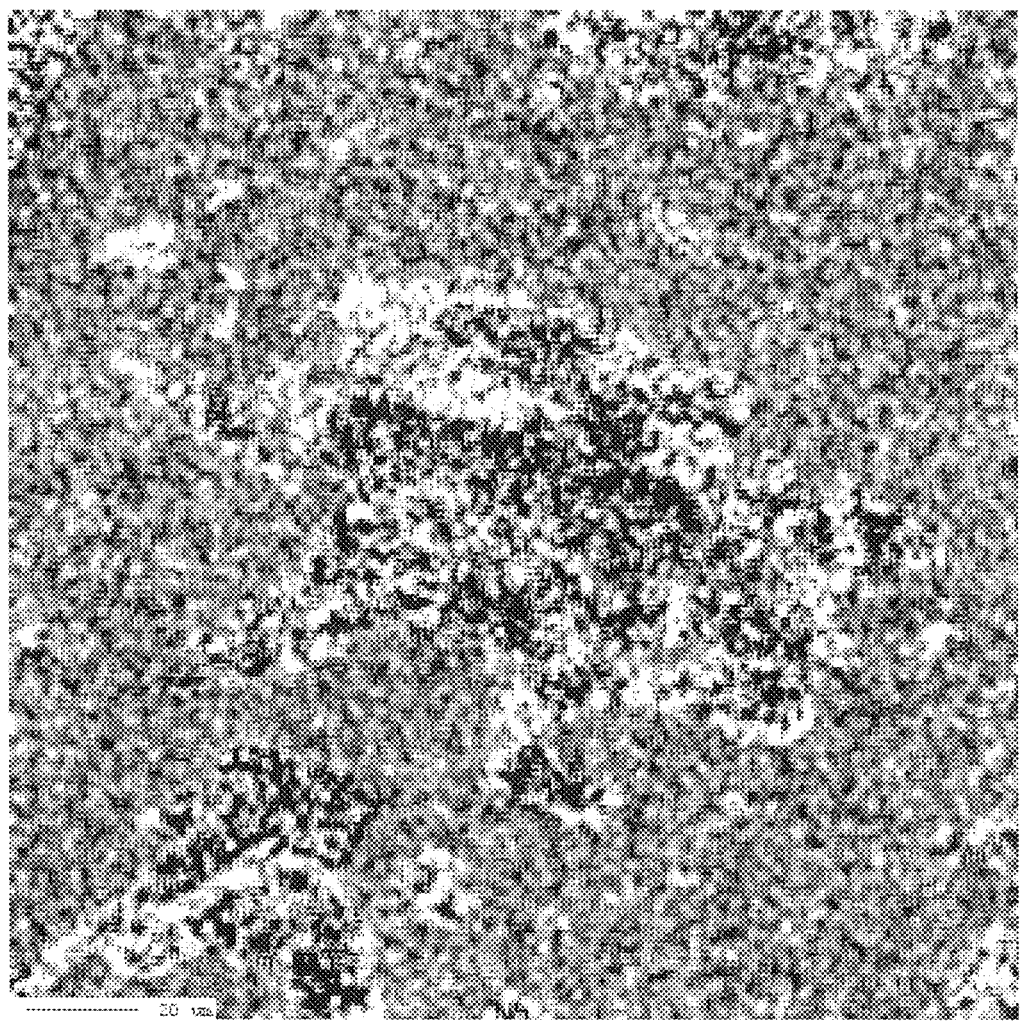
FIG. 12 illustrates principal component score map data of a ninth principal component score.
Figure 13:
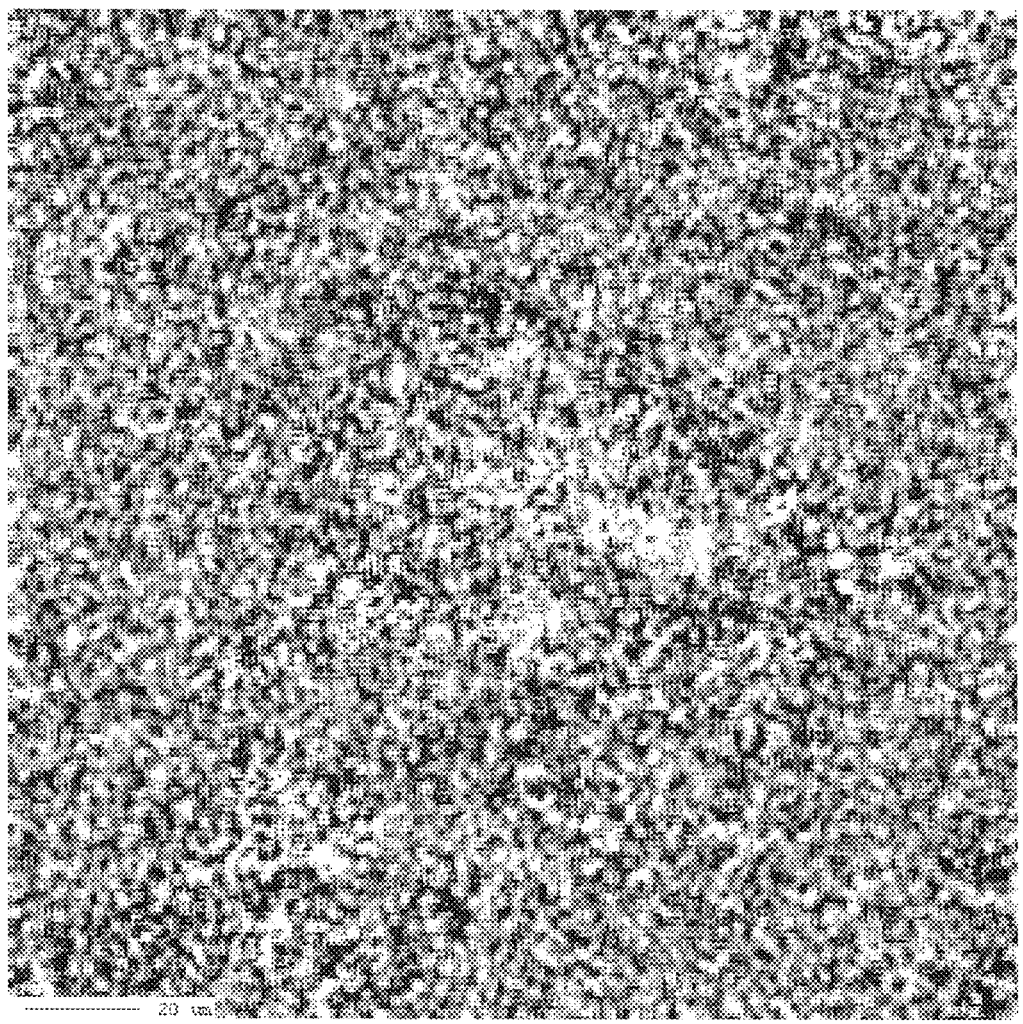
FIG. 13 illustrates principal component score map data of a tenth principal component score.

The principal component analysis section 112 generates the principal component score map data as described above corresponding to the second to tenth principal components. FIG. 5 illustrates principal component score map data of the second principal component score. FIG. 6 illustrates principal component score map data of the third principal component score. FIG. 7 illustrates principal component score map data of the fourth principal component score. FIG. 8 illustrates principal component score map data of the fifth principal component score. FIG. 9 illustrates principal component score map data of the sixth principal component score. FIG. 10 illustrates principal component score map data of the seventh principal component score. FIG. 11 illustrates principal component score map data of the eighth principal component score. FIG. 12 illustrates principal component score map data of the ninth principal component score. FIG. 13 illustrates principal component score map data of the tenth principal component score.

The scatter diagram generation section 113 plots the calculated principal component score to generate a principal component score scatter diagram. Specifically, the scatter diagram generation section 113 selects the principal component having a large eigenvalue. The scatter diagram generation section 113 selects the principal component so that the cumulative contribution ratio is equal to or larger than a predetermined value (e.g., 80%), for example. In the example illustrated in FIG. 3, since the cumulative contribution ratio corresponding to the second principal component exceeds 80%, the scatter diagram generation section 113 selects the first principal component and the second principal component. Note that the scatter diagram generation section 113 may select the principal component having an eigenvalue equal to or larger than 1, or may select the principal component having a contribution ratio equal to or larger than a predetermined value.

Figure 14:
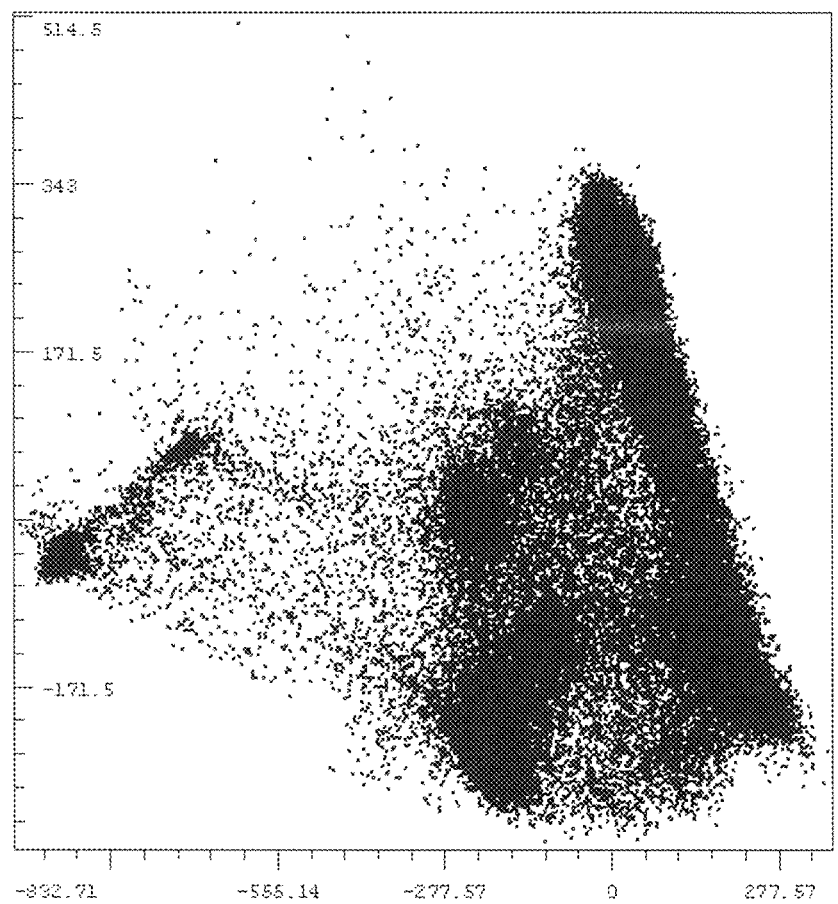
FIG. 14 illustrates an example of a principal component score scatter diagram.

The scatter diagram generation section 113 generates the principal component score scatter diagram using the selected principal component. For example, when the scatter diagram generation section 113 has selected the first principal component and the second principal component, the scatter diagram generation section 113 plots the first principal component score and the second principal component score (that correspond to each pixel of the elemental map data) on a scatter diagram in which the horizontal axis indicates the first principal component score, and the vertical axis indicates the second principal component score. The scatter diagram generation section 113 thus generates the principal component score scatter diagram. FIG. 14 is a view illustrating an example of the principal component score scatter diagram. In the scatter diagram illustrated in FIG. 14, the horizontal axis indicates the first principal component score, and the vertical axis indicates the second principal component score.

Although an example in which the scatter diagram generation section 113 selects the first principal component and the second principal component, and generates the two-dimensional scatter diagram has been described above, the scatter diagram generation section 113 may select the first to nth (n<N) principal components, and generate an n-dimensional scatter diagram.

The peak position detection section 114 detects the peak position from the principal component score scatter diagram. The peak position is the center-of-gravity position of each cluster (group) (i.e., the representative position of each cluster) within the principal component score scatter diagram. For example, the peak position detection section 114 divides the principal component score scatter diagram into a plurality of areas, counts the number of data points within each area to calculate the point density, and detects the peak position based on the point density. The peak position detection section 114 determines an area among the contiguous areas that has the highest point density to be a peak position candidate, and determines the peak position candidate to be the peak position when the point density is equal to or higher than a threshold value, for example. The process performed by the peak position detection section 114 is described in detail below.

Figure 15:
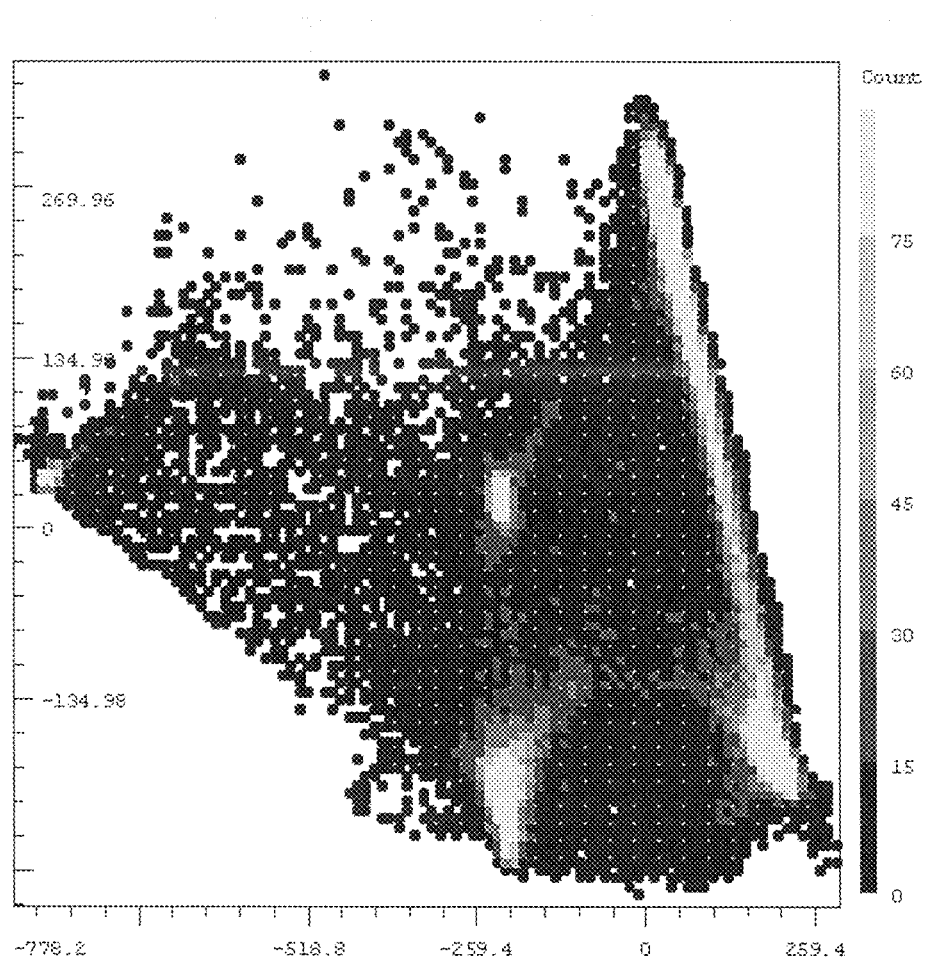
FIG. 15 illustrates a principal component score scatter diagram that is displayed using point density.

The peak position detection section 114 performs a process that displays the principal component score scatter diagram generated by the scatter diagram generation section 113 using the point density. FIG. 15 is a view illustrating the principal component score scatter diagram that is displayed using the point density. In the example illustrated in FIG. 15, the principal component score scatter diagram illustrated in FIG. 14 is divided into 100×100 areas, and the number of data points (point density) that has been counted within each area is displayed. In FIG. 15, the point density (i.e., the number of data points) is indicated by shading.

Figure 16:
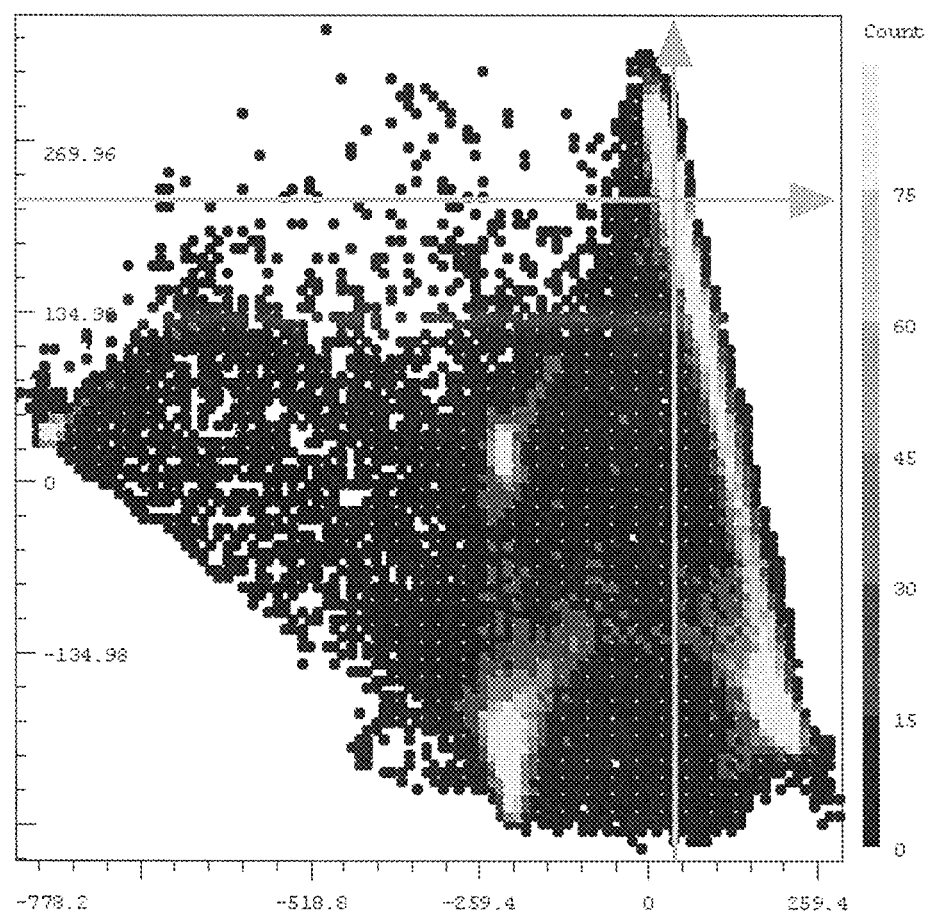
FIG. 16 illustrates part of data (horizontal axis direction) of a scatter diagram displayed using point density.

As illustrated in FIG. 16, the peak position detection section 114 searches the scatter diagram (displayed using the point density) for the peak position in the horizontal axis direction. When the peak position detection section 114 searches the scatter diagram in the horizontal axis direction, the peak position detection section 114 determines an area in which the number of data points is larger than that of the areas contiguous thereto in the horizontal axis direction to be the peak position. FIG. 17 illustrates part of the data of the scatter diagram displayed using the point density. In FIG. 17, each value represents the number of data points.

When the peak position detection section 114 has found an area that is considered to be the peak position by searching the scatter diagram in the horizontal axis direction, the peak position detection section 114 searches the scatter diagram for the peak position in the vertical axis direction so as to pass through the area (considered to be the peak position) that has been found by searching the scatter diagram in the horizontal axis direction. When the peak position detection section 114 searches the scatter diagram in the vertical axis direction, the peak position detection section 114 determines an area in which the number of data points is larger than that of the areas contiguous thereto in the vertical axis direction to be the peak position. The peak position detection section 114 determines an area (indicated by the diagonal lines that extend from upper right to lower left in FIG. 17) that has been determined to be the peak position by both the search process in the horizontal axis direction and the search process in the vertical axis direction to be a peak position candidate.

The peak position detection section 114 performs the above process on the entire scatter diagram (displayed using the point density) in order to find a peak position candidate. In the example illustrated in FIG. 17, five areas have been determined to be a peak position candidate.

Note that the peak position detection section 114 may perform a process that smoothens the scatter diagram (displayed using the point density) before performing the process that searches the scatter diagram for a peak position candidate. This makes it possible to reduce the probability that two contiguous peaks have the same value (i.e., the same number of data points).

The peak position detection section 114 then performs a narrow-down process on the peak position candidates that have been found by the above process. The peak position detection section 114 passes over a peak position candidate among the peak position candidates that have been found by the above process in which the number of data points is less than a threshold value. Specifically, the peak position detection section 114 determines (selects) a peak position candidate among the peak position candidates that have been found by the above process in which the number of data points is equal to or larger than the threshold value to be the peak position. The threshold value may be arbitrarily set. For example, the threshold value is set to ⅕th of the maximum number of data points. Note that the threshold value may be set to (corresponding to) the maximum number of data points.

When an area in which the number of data points is larger than that of the peak position candidate is present at a position close to the peak position candidate (e.g., within the range of five areas around the peak position candidate), the peak position detection section 114 may pass over the peak position candidate. This makes it possible to prevent a situation in which a plurality of peak positions are situated within a narrow range.

The peak position detection section 114 thus detects the peak position from the principal component score scatter diagram. In the example illustrated in FIG. 17, the peak position detection section 114 has determined the area indicated by both the diagonal lines that extend from upper right to lower left and the diagonal lines that extend from upper left to lower right to be the peak position.

The peak position detection section 114 detects a plurality of peak positions from the principal component score scatter diagram. In the example illustrated in FIG. 15, the peak position detection section 114 detects five peak positions.

The clustering section 115 calculates the distance between each point and each peak position within the principal component score scatter diagram, and classifies each point within the principal component score scatter diagram into a plurality of groups based on the calculated distance. For example, the clustering section 115 classifies each point within the principal component score scatter diagram so that each point belongs to the group (cluster) that corresponds to the peak position that is situated at the shortest distance from each point.

Figure 18:
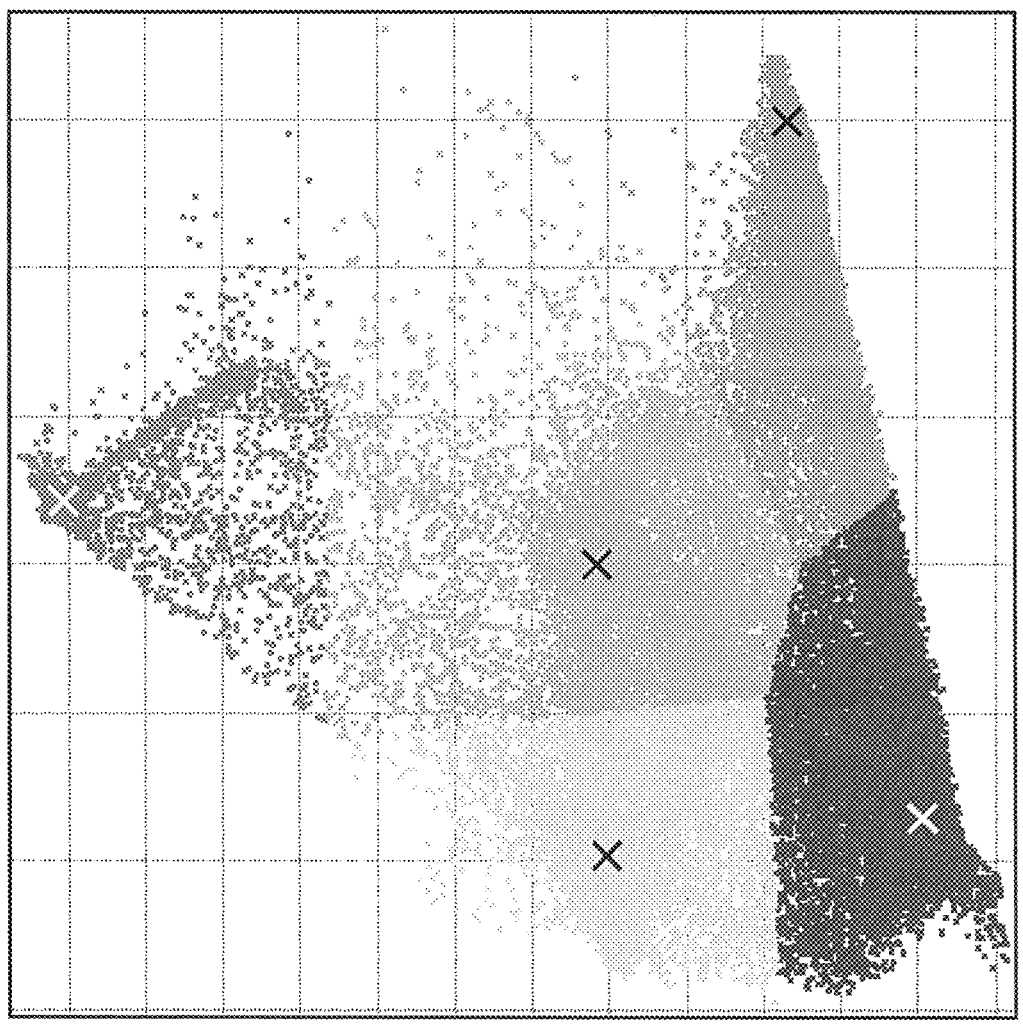
FIG. 18 illustrates a principal component score scatter diagram that is color-coded corresponding to each group.

FIG. 18 is a view illustrating the principal component score scatter diagram that is color-coded corresponding to each group. In the example illustrated in FIG. 18, each group is indicated by shading. In FIG. 18, each symbol "×" indicates the peak position. The clustering section 115 calculates the Euclidean distance between each point and each peak position within the principal component score scatter diagram, and classifies each point within the principal component score scatter diagram so that each point belongs to the group that corresponds to the peak position that is situated at the shortest distance from each point. In the example illustrated in FIG. 18, the clustering section 115 classifies each point within the principal component score scatter diagram into five groups since five peak positions have been detected by the peak position detection section 114.

For example, the clustering section 115 classifies each point within the principal component score scatter diagram so that each point belongs to one of the groups. Note that the clustering section 115 may not classify a point within the principal component score scatter diagram that is situated at a distance longer than a predetermined value with respect to each peak position. For example, the clustering section 115 does not classify a point (outlier point) that is situated at a distance longer than a value obtained by multiplying the sigma value of each peak position by alpha (alpha is an arbitrary number). The clustering section 115 may be configured to operate in a mode in which the clustering section 115 classifies each point within the scatter diagram to belong to one of the groups, or a mode in which the clustering section 115 does not classify an outlier point. The device (analyzer) may be configured so that the user can switch the operation mode of the clustering section 115 between these modes.

Figure 19:
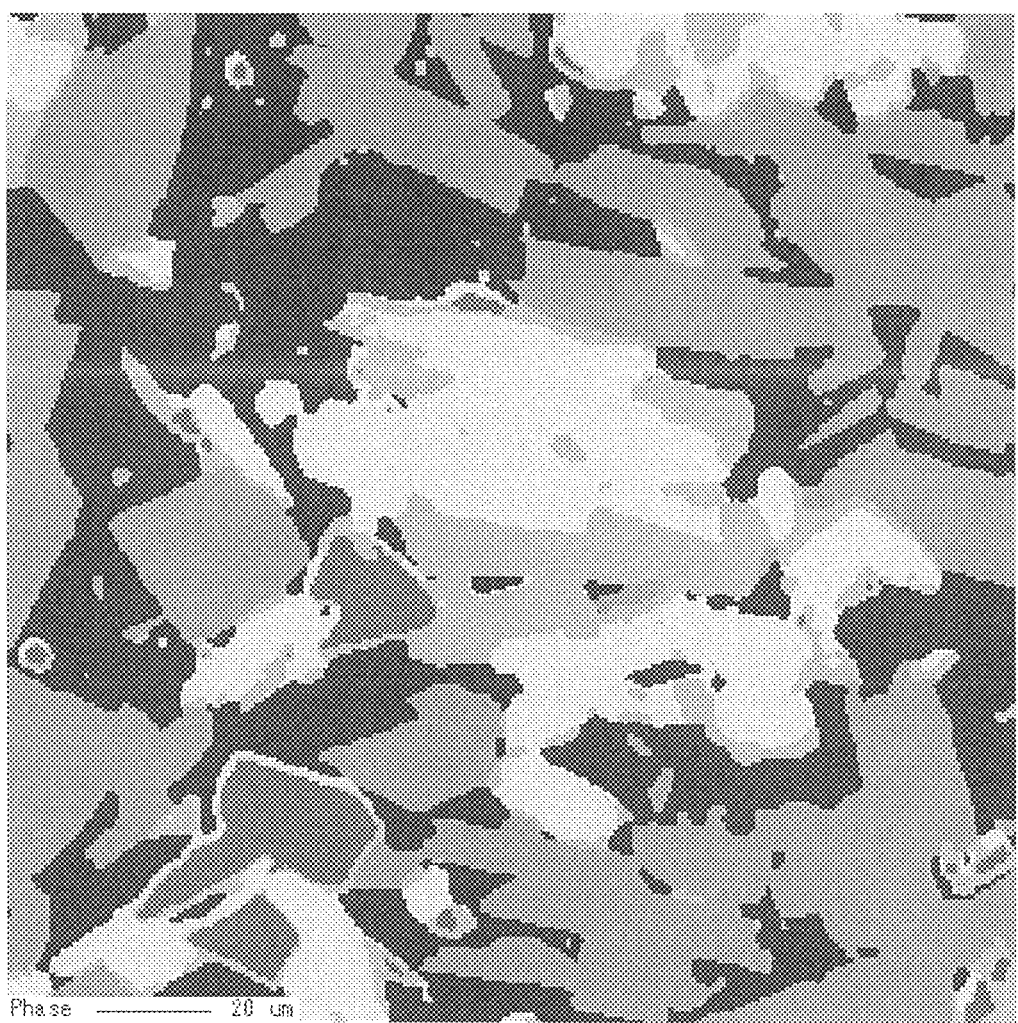
FIG. 19 illustrates an example of a phase map generated by a phase map generation section.

The phase map generation section 116 generates the phase map based on the classification results of the clustering section 115. The phase map generation section 116 returns each point within the principal component score scatter diagram that is color-coded corresponding to each group to the corresponding pixel (unit area) of the elemental map data to generate the phase map in the form of elemental map data. FIG. 19 is a view illustrating an example of the phase map generated by the phase map generation section 116. As illustrated in FIG. 19, the phase map represents the distribution of the groups (clusters).

The phase map generation section 116 may apply a label corresponding to the composition to each (color-coded) group within the phase map. For example, the phase map generation section 116 may display the elements included in the phase (in descending order of the ratio) corresponding to each group. The phase map generated by the phase map generation section 116 is displayed on the display section 122, for example.

The phase analyzer 100 has the following features, for example.

The phase analyzer 100 includes the principal component analysis section 112 that performs the principal component analysis on the elemental map data that represents the intensity or concentration distribution corresponding to each element to calculate the principal component score corresponding to each unit area of the elemental map data, the scatter diagram generation section 113 that plots the calculated principal component score to generate the scatter diagram of the principal component score, the peak position detection section 114 that detects the peak position from the principal component score scatter diagram, the clustering section 115 that calculates the distance between each point and each peak position within the principal component score scatter diagram, and classifies each point within the principal component score scatter diagram into a plurality of groups based on the calculated distance, and the phase map generation section 116 that generates the phase map based on the classification results of the clustering section 115. Therefore, the user need not select an appropriate combination of elements from a large number of elements and determine the correlation between the elements, and it is possible to easily generate the phase map.

Since the phase analyzer 100 utilizes the principal component analysis, it is possible to easily generate the phase map while utilizing information about a larger number of elements as compared with the case of selecting a small number of elements from a large number of elements, and performing phase analysis based on the correlation between the selected elements.

The peak position detection section 114 divides the principal component score scatter diagram into a plurality of areas, counts the number of data points within each area to calculate the point density, and detects the peak position based on the point density. This makes it possible to detect the peak position (i.e., the center of gravity of each cluster) from the principal component score scatter diagram.

The peak position detection section 114 determines an area among the contiguous areas within the principal component score scatter diagram that has the highest point density to be a peak position candidate, and determines (selects) the peak position candidate in which the point density is equal to or higher than a threshold value to be the peak position. This makes it possible to perform the peak position narrow-down process.

The clustering section 115 classifies each point within the principal component score scatter diagram so that each point belongs to the group that corresponds to the peak position that is situated at the shortest distance from each point. This makes it possible to classify each point within the principal component score scatter diagram corresponding to the composition.

The phase map generation section 116 displays the phase map on the display section 122 in a state in which each point within the phase map is color-coded corresponding to each group. Therefore, the phase analyzer 100 can comprehensibly display the phase distribution.

Since the surface analyzer 1000 includes the phase analyzer 100, the surface analyzer 1000 can easily generate the phase map.

2. Phase Analysis Method

Figure 20:
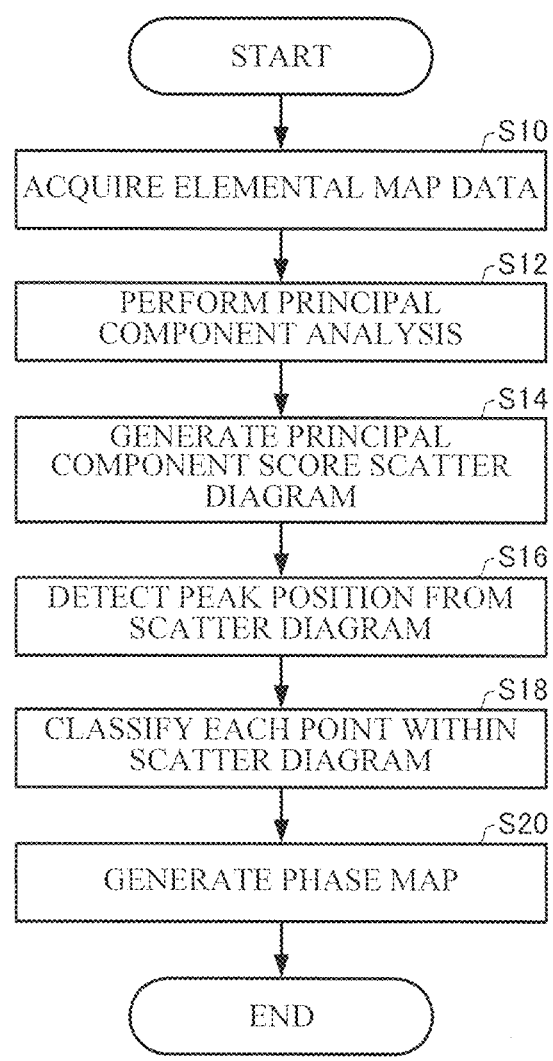
FIG. 20 is a flowchart illustrating an example of a phase analysis method according to one embodiment of the invention.
Figure 21:
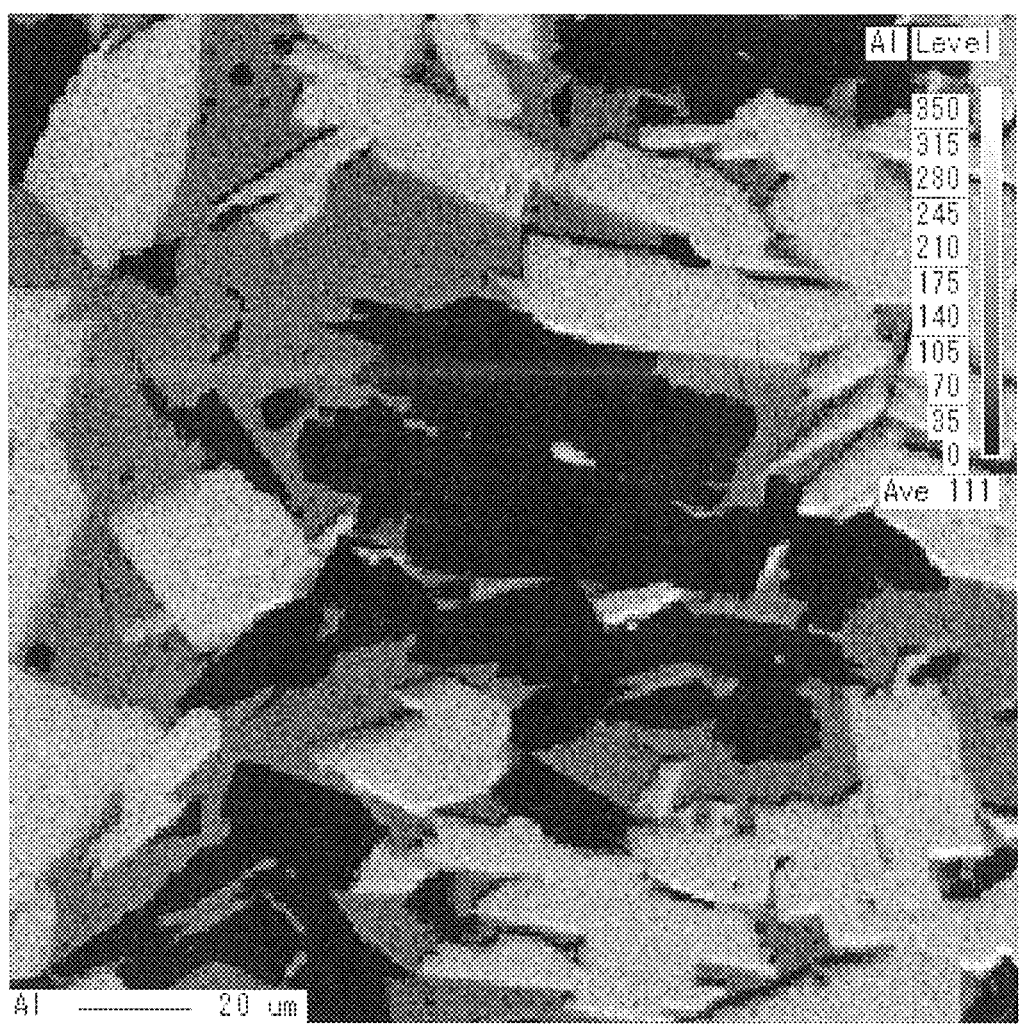
FIG. 21 illustrates Al elemental map data.
Figure 22:
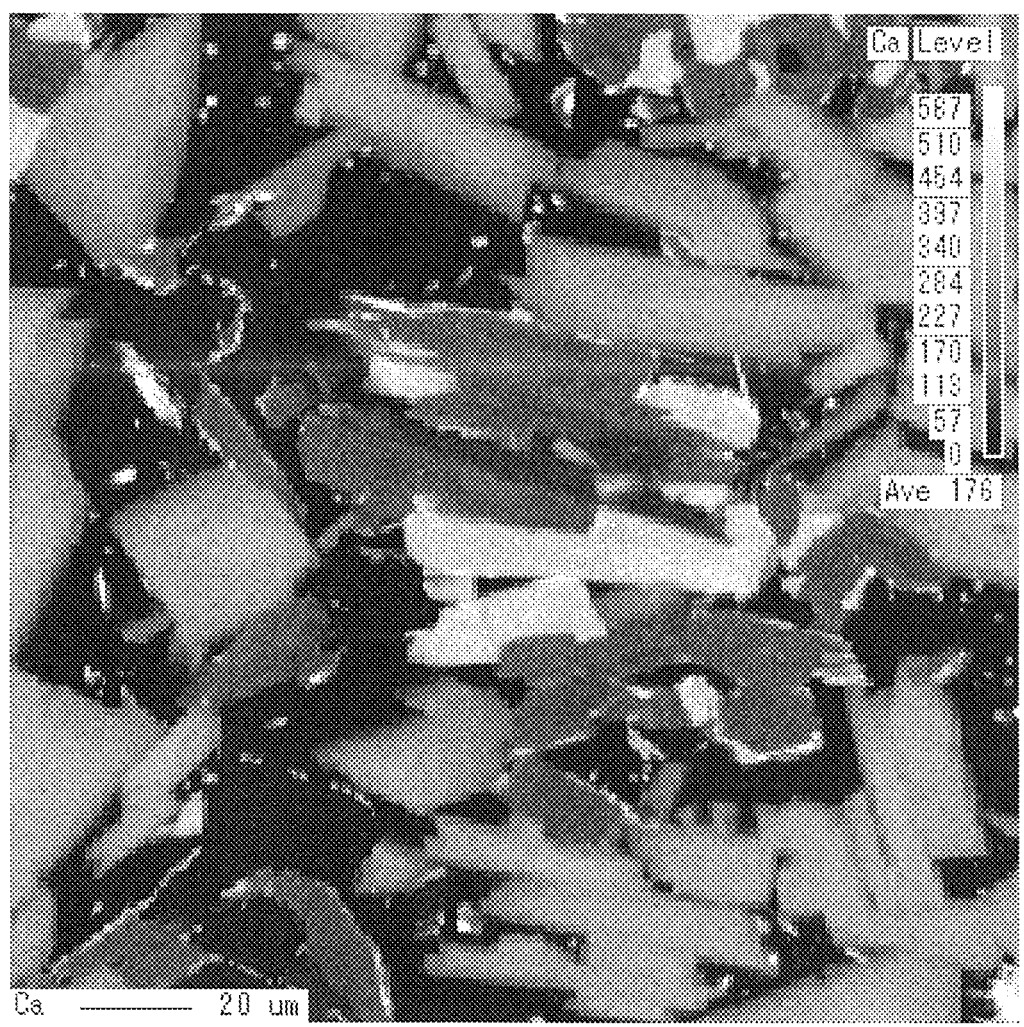
FIG. 22 illustrates Ca elemental map data.
Figure 23:
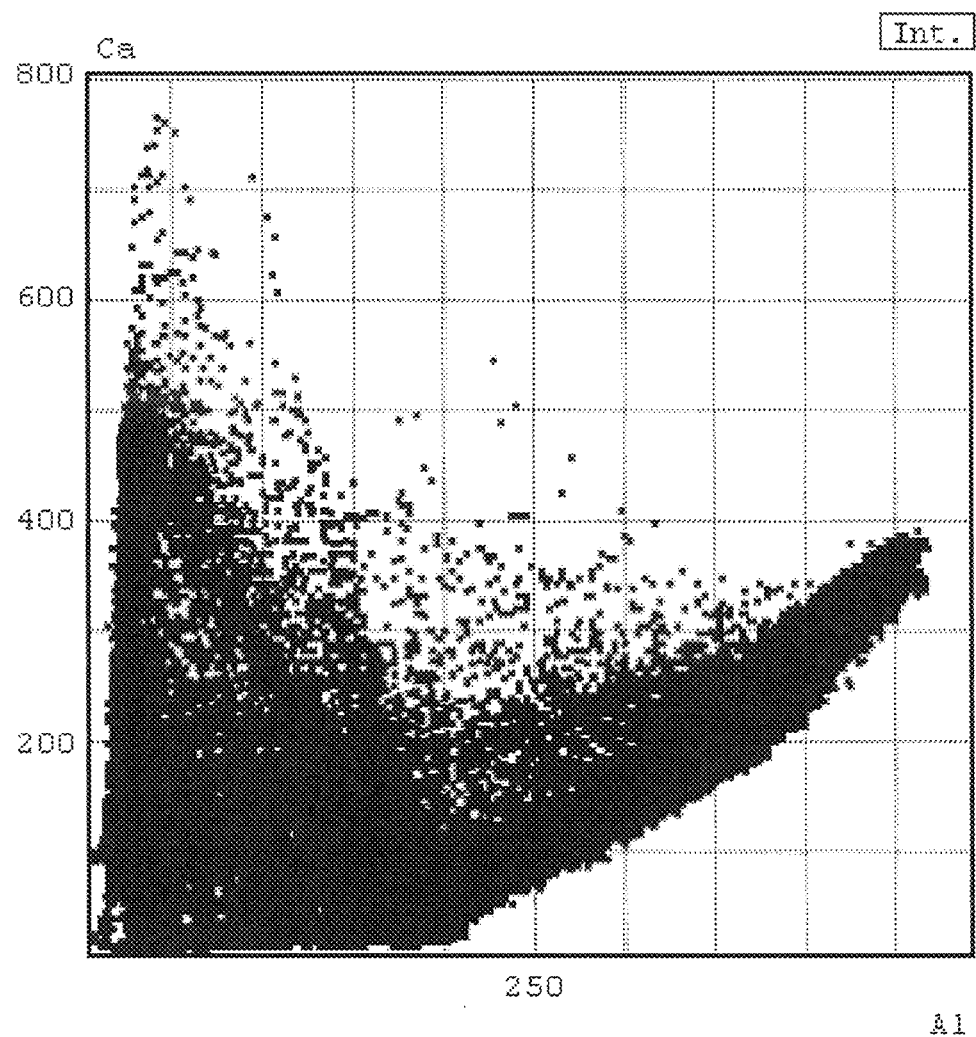
FIG. 23 illustrates a scatter diagram in which the horizontal axis indicates Al elemental map data, and the vertical axis indicates Ca elemental map data.
Figure 24:
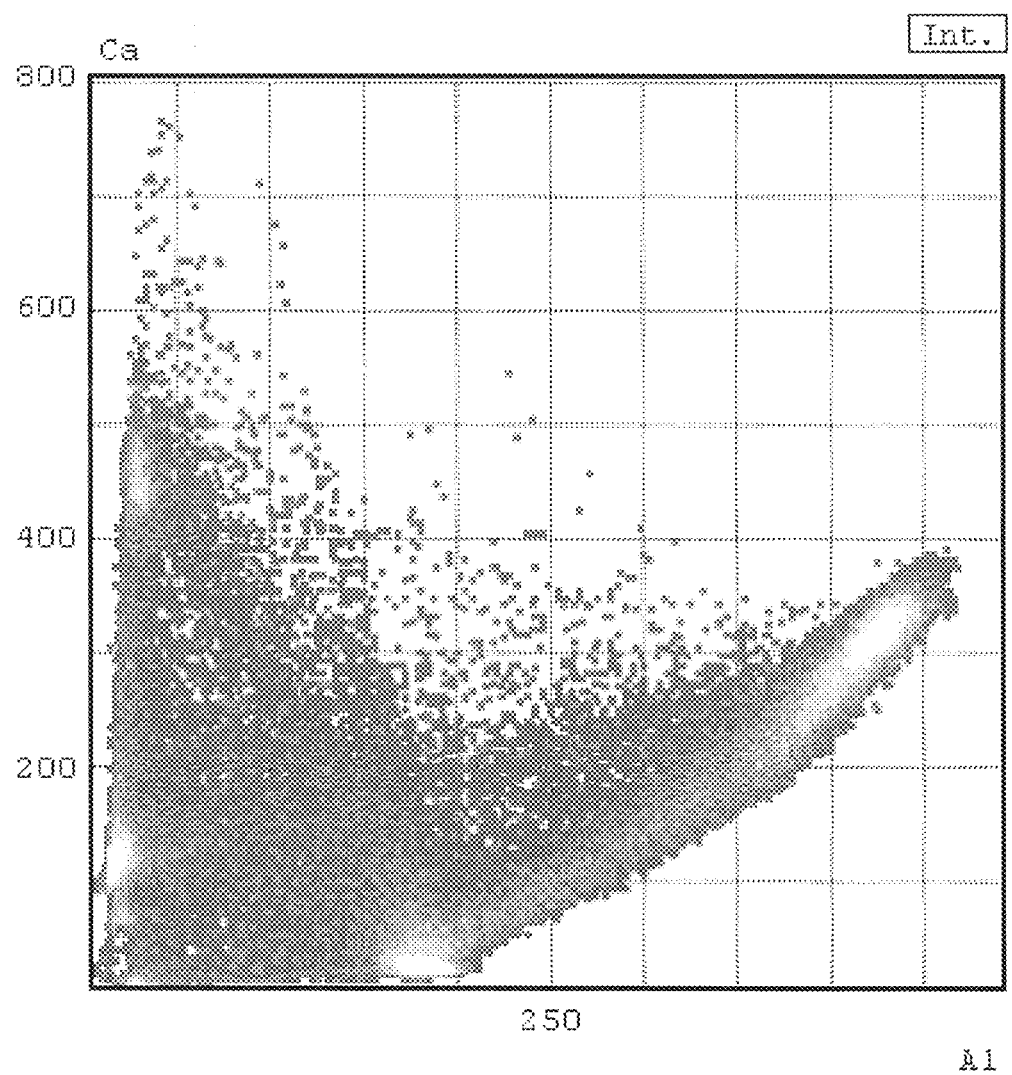
FIG. 24 illustrates a scatter diagram in which the display color is changed corresponding to the number of data points.
Figure 25:
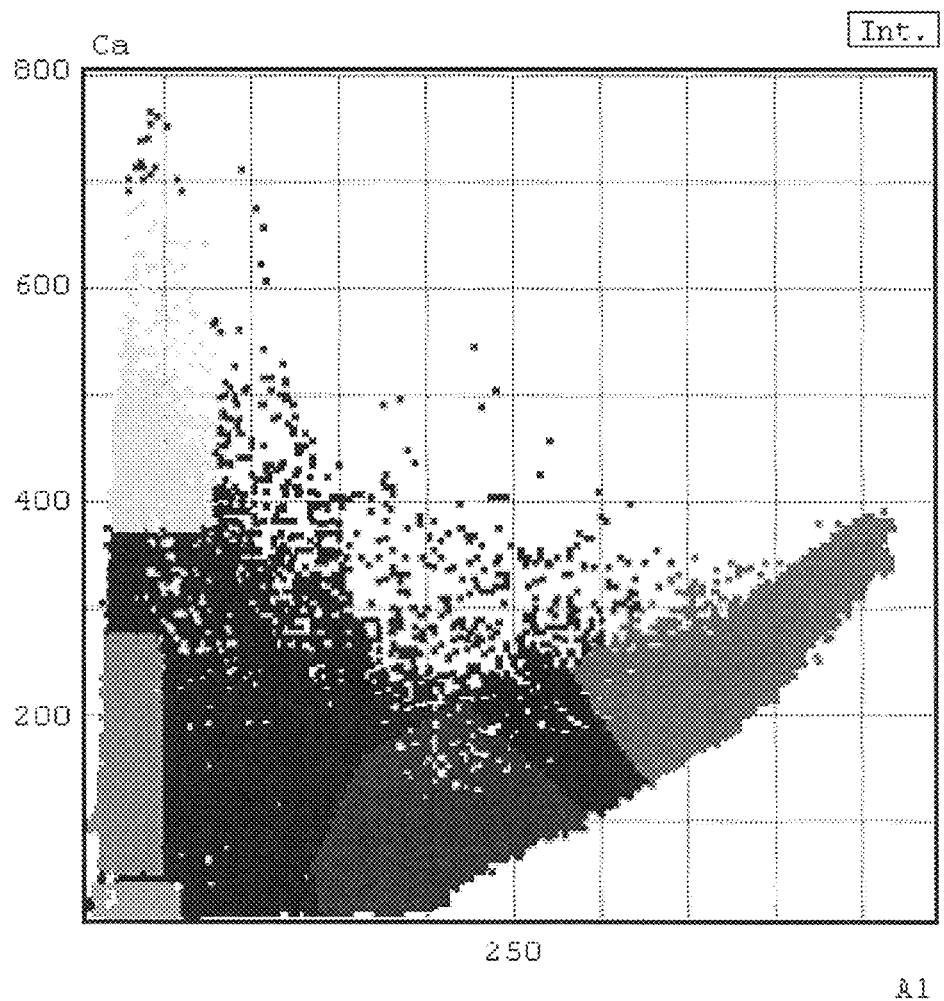
FIG. 25 illustrates a scatter diagram in which each uneven distribution is enclosed, and a different color is applied to each uneven distribution.
Figure 26:
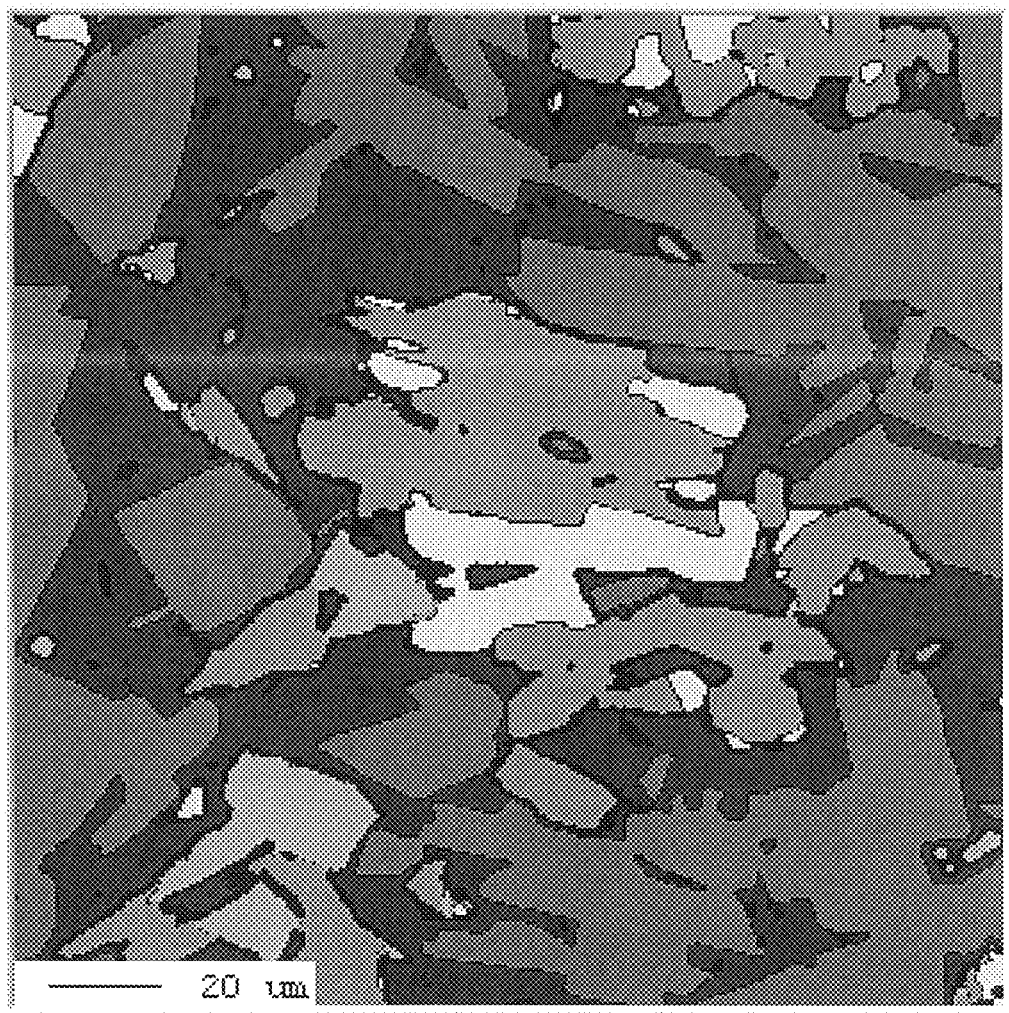
FIG. 26 illustrates an example of a phase map.

A phase analysis method according to one embodiment of the invention is described below with reference to the drawings. FIG. 20 is a flowchart illustrating an example of the phase analysis method according to one embodiment of the invention. A phase analysis method that utilizes the phase analyzer 100 is described below as an example of the phase analysis method according to one embodiment of the invention.

The elemental map data acquisition section 111 acquires a plurality of pieces of elemental map data (step S10). For example, the user selects the Al elemental map data, the Ca elemental map data, the O elemental map data, the Si elemental map data, the Mn elemental map data, the Fe elemental map data, the Ni elemental map data, the Ti elemental map data, the Mg elemental map data, and the Cr elemental map data illustrated in FIG. 2, and the elemental map data acquisition section 111 acquires the Al elemental map data, the Ca elemental map data, the O elemental map data, the Si elemental map data, the Mn elemental map data, the Fe elemental map data, the Ni elemental map data, the Ti elemental map data, the Mg elemental map data, and the Cr elemental map data.

The principal component analysis section 112 performs the principal component analysis on the elemental map data to calculate the principal component score corresponding to each pixel (unit area) of the elemental map data (step S12). The information about the contribution ratio, the cumulative contribution ratio, the eigenvalue, and the eigenvector (see FIG. 3) is obtained corresponding to each principal component as a result of the principal component analysis performed by the principal component analysis section 112.

The principal component analysis section 112 calculates the principal component score corresponding to each pixel of each elemental map data using the eigenvector (see FIG. 3) to generate the principal component score map data corresponding to each principal component (see FIGS. 4 to 13).

The scatter diagram generation section 113 plots the calculated principal component score to generate the principal component score scatter diagram (step S14). For example, the scatter diagram generation section 113 selects the first principal component and the second principal; component by which the cumulative contribution ratio is 80% or more, and plots the principal component score of the first principal component and the principal component score of the second principal component to generate the principal component score scatter diagram (see FIG. 14).

The peak position detection section 114 detects the peak position from the principal component score scatter diagram (step S16). The peak position detection section 114 divides the principal component score scatter diagram into a plurality of areas, counts the number of data points within each area to calculate the point density (see FIG. 15), and detects the peak position based on the point density. The peak position detection section 114 determines an area among the contiguous areas that has the highest point density to be a peak position candidate, and determines the peak position candidate in which the point density is equal to or higher than a threshold value to be the peak position. The peak position detection section 114 detects five peak positions from the scatter diagram illustrated in FIG. 15 (that is displayed using the point density).

The clustering section 115 calculates the distance between each point and each peak position within the principal component score scatter diagram, and classifies each point within the principal component score scatter diagram into a plurality of groups based on the calculated distance (step S18). The clustering section 115 classifies each point within the principal component score scatter diagram so that each point belongs to the group (cluster) that corresponds to the peak position that is situated at the shortest distance from each point (see FIG. 18). The clustering section 115 classifies (and color-codes) each point within the principal component score scatter diagram into five clusters (groups) that respectively correspond to the five peak positions (see FIG. 18).

The phase map generation section 116 generates the phase map based on the classification results of the clustering section 115 (step S20). The phase map generation section 116 returns each point within the principal component score scatter diagram (that is color-coded) to the corresponding pixel (unit area) of the elemental map data to generate the phase map in the font of elemental map data (see FIG. 19). The phase map generation section 116 thus generates the phase map. The phase map generation section 116 displays the phase map on the display section 122 in a state in which each point within the phase map is color-coded corresponding to each group.

The phase analysis method according to one embodiment of the invention has the following features, for example.

The phase analysis method according to one embodiment of the invention includes a principal component analysis step that performs the principal component analysis on the elemental map data that represents the intensity or concentration distribution corresponding to each element to calculate the principal component score corresponding to each unit area of the elemental map data (step S12), a scatter diagram generation step that plots the calculated principal component score to generate the principal component score scatter diagram (step S14), a peak position detection step that detects the peak position from the principal component score scatter diagram (step S16), a clustering step that calculates the distance between each point and each peak position within the principal component score scatter diagram, and classifies each point within the principal component score scatter diagram into a plurality of groups based on the calculated distance (step S18), and a phase map generation step that generates the phase map based on the classification results of the clustering step (step S20). Therefore, the user need not select an appropriate combination of elements from a large number of elements and determine the correlation between the elements, and it is possible to easily generate the phase map.

Since the phase analysis method according to one embodiment of the invention utilizes the principal component analysis, it is possible to easily generate the phase map while utilizing information about a larger number of elements as compared with the case of selecting a small number of elements from a large number of elements, and performing phase analysis based on the correlation between the selected elements.

In the peak position detection step, the principal component score scatter diagram is divided into a plurality of areas, the number of data points within each area is counted to calculate the point density, and the peak position is detected based on the point density. This makes it possible to detect the peak position (i.e., the center of gravity of each cluster) from the principal component score scatter diagram.

In the peak position detection step, an area among the contiguous areas within the principal component score scatter diagram that has the highest point density is determined to be a peak position candidate, and the peak position candidate in which the point density is equal to or higher than a threshold value is determined (selected) to be the peak position. This makes it possible to perform the peak position narrow-down process in the peak position detection step.

In the clustering step, each point within the principal component score scatter diagram is classified so that each point belongs to the group that corresponds to the peak position that is situated at the shortest distance from each point. This makes it possible to classify each point within the principal component score scatter diagram corresponding to the composition in the clustering step.

In the phase map generation step, the phase map is displayed on the display section 122 in a state in which each point within the phase map is color-coded corresponding to each group. This makes it possible to comprehensibly display the phase distribution on the display section 122.

The invention is not limited to the above embodiments. Various modifications and variations may be made of the above embodiments without departing from the scope of the invention.

Although the above embodiments illustrate an example in which the surface analyzer 1000 is an electron probe microanalyzer (EPMA), the surface analyzer is not limited to an electron probe microanalyzer (EPMA) as long as the surface analyzer is a device that can acquire elemental map data. For example, the surface analyzer may be a scanning transmission electron microscope (SEM) that is provided with an Auger electron spectroscope, an X-ray photoelectron spectroscope (XPS), an energy dispersive X-ray spectrometer (EDS), or the like.

Although the above embodiments illustrate an example in which the phase analyzer 100 is included in the surface analyzer 1000, the phase analyzer need not necessarily be included in the surface analyzer. For example, the phase analyzer may acquire the elemental map data through the information storage medium 126, and perform the phase analysis.

The invention includes various other configurations substantially the same as the configurations described in connection with the above embodiments (e.g., a configuration having the same function, method, and results, or a configuration having the same objective and effects). The invention also includes a configuration in which an unsubstantial element (part) described in the embodiments is replaced by another element (part). The invention also includes a configuration having the same effects as those of the configurations described in connection with the above embodiments, or a configuration capable of achieving the same objective as that of the configurations described in connection with the above embodiments. The invention further includes a configuration in which a known technique is added to the configurations described in connection with the above embodiments.

Although only some embodiments of the invention have been described in detail above, those skilled in the art would readily appreciate that many modifications are possible in the embodiments without materially departing from the novel teachings and advantages of the invention. Accordingly, all such modifications are intended to be included within the scope of the invention.

What is claimed is:

1. A phase analyzer comprising:
a principal component analysis section that performs principal component analysis on N items of elemental map data that represents an intensity or concentration distribution corresponding to each element and obtains information about N principal components to calculate a principal component score corresponding to each pixel of the elemental map data from the obtained information about the N principal components;
a scatter diagram generation section that selects at least two principal components having larger eigenvalues from among the N principal components and plots a point corresponding to the pixel on a coordinate system with coordinate axes indicating principal component scores of the selected principal components to generate a scatter diagram of the principal component score;
a peak position detection section that divides the scatter diagram into a plurality of areas, counts a number of data points within each of the plurality of areas to calculate a point density, and detects a peak position based on the point density;
a clustering section that calculates an Euclidean distance between each point and each peak position within the scatter diagram, and classifies each point within the scatter diagram into a plurality of groups based on the distance; and
a phase map generation section that generates a phase map by providing a color to each point within the scatter diagram when the color is different for each group of the plurality of groups, and by reflecting the color provided to each point within the scatter diagram on the color of each pixel of the elemental map corresponding to each point within the scatter diagram.

2. The phase analyzer as defined in claim 1,
wherein the peak position detection section determines an area among contiguous areas included in the plurality of areas that has a highest point density to be a peak position candidate, and selects the peak position candidate in which the point density is equal to or higher than a threshold value to be the peak position.

3. The phase analyzer as defined in claim 1,
wherein the clustering section classifies each point within the scatter diagram so that each point belongs to a group among the plurality of groups that corresponds to the peak position that is situated at a shortest distance from each point.

4. A phase analysis method comprising:
a principal component analysis step that performs principal component analysis on N items of elemental map data that represents an intensity or concentration distribution corresponding to each element and obtains information about N principal components to calculate a principal component score corresponding to each pixel of the elemental map data from the obtained information about the N principal components;
a scatter diagram generation step that selects at least two principal components having larger eigenvalues from among the N principal components and plots a point corresponding to the pixel on a coordinate system with coordinate axes indicating principal component scores of the selected principal components to generate a scatter diagram of the principal component score;
a peak position detection step that divides the scatter diagram into a plurality of areas, counts a number of data points within each of the plurality of areas to calculate a point density, and detects a peak position based on the point density;
a clustering step that calculates an Euclidean distance between each point and each peak position within the scatter diagram, and classifies each point within the scatter diagram into a plurality of groups based on the distance; and
a phase map generation step that generates a phase map by providing a color to each point within the scatter diagram when the color is different for each group of the plurality of groups, and by reflecting the color provided to each point within the scatter diagram on the color of each pixel of the elemental map corresponding to each point within the scatter diagram.

5. The phase analysis method as defined in claim 4,
wherein the peak position detection step determines an area among contiguous areas included in the plurality of areas that has a highest point density to be a peak position candidate, and selects the peak position candidate in which the point density is equal to or higher than a threshold value to be the peak position.

6. The phase analysis method as defined in claim 4,
wherein the clustering step classifies each point within the scatter diagram so that each point belongs to a group among the plurality of groups that corresponds to the peak position that is situated at a shortest distance from each point.

7. A surface analyzer comprising the phase analyzer as defined in claim 1.

* * * * *